United States Patent
Burnside et al.

(10) Patent No.: US 6,578,579 B2
(45) Date of Patent: *Jun. 17, 2003

(54) SYSTEMS AND METHODS FOR PREVENTING AUTOMATIC IDENTIFICATION OF RE-USED SINGLE USE DEVICES

(75) Inventors: Robert R. Burnside, Mountain View, CA (US); Bruce Wand, San Jose, CA (US); David K. Swanson, Mountain View, CA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 66 days.

This patent is subject to a terminal disclaimer.

(21) Appl. No.: 09/850,849

(22) Filed: May 7, 2001

(65) Prior Publication Data
US 2001/0018918 A1 Sep. 6, 2001

Related U.S. Application Data

(63) Continuation of application No. 09/391,109, filed on Sep. 7, 1999, now Pat. No. 6,237,604.
(51) Int. Cl.[7] .............................................. A61B 19/00
(52) U.S. Cl. ................................................... 128/897
(58) Field of Search ............................ 128/897; 606/1, 606/10, 11, 12, 32, 33, 34, 35, 41, 42, 45, 46, 47, 48, 49, 50; 600/300

(56) References Cited

U.S. PATENT DOCUMENTS

| 5,383,874 | A | 1/1995 | Jackson et al. |
| 5,400,267 | A | 3/1995 | Denen et al. |
| 5,425,375 | A | 6/1995 | Chin et al. |
| 5,487,386 | A | 1/1996 | Wakabayashi et al. |
| 5,991,355 | A | 11/1999 | Dahlke |
| 6,055,453 | A | 4/2000 | Hofmann et al. |
| 6,237,604 | B1 * | 5/2001 | Burnside et al. ............ 128/897 |

FOREIGN PATENT DOCUMENTS

WO    WO 93/20770    10/1993

* cited by examiner

Primary Examiner—Max F. Hindenburg
Assistant Examiner—Brian Szmal
(74) Attorney, Agent, or Firm—Bingham McCutchen LLP

(57) ABSTRACT

A medical system for limiting the re-use of a medical probe, such as, e.g., a catheter or a surgical probe, is provided. The medical system includes a medical probe that includes an electronic storage component for storing a probe identification code. The medical probe further includes a disabling circuit, the activation of which disables the electronic storage component. The medical system further includes a control unit, such as, e.g., an RF generator, for connection to the medical probe. The control unit includes control circuit that is configured for automatically reading the probe identification code from the electronic storage component and preventing the medical probe from being operated if the probe identification code is not approved. If the medical probe has been previously used, the control circuit prevents operation of the medical probe and activates the disabling circuitry to disable the electronic storage component in the medical probe.

23 Claims, 11 Drawing Sheets

SYSTEMS AND METHODS FOR PREVENTING AUTOMATIC IDENTIFICATION OF RE-USED SINGLE USE DEVICES

This is a continuation of application Ser. No. 09/391,109 filed Sep. 7, 1999 now U.S. Pat. No. 6,237,604.

FIELD OF THE INVENTION

The present invention is directed to medical systems, and more specifically, to systems, apparatus and methods for limiting the re-usage of medical probes, such as catheters and surgical probes.

BACKGROUND

Catheters, surgical probes and related probe devices (collectively referred to, hereinafter, as "medical probes" or "probes") are used today in diagnostic and therapeutic medical procedures that require surgical or minimally invasive access to target tissue areas within interior regions of the body. During these procedures, a physician locates the distal end of the medical probe at the target site by, in the case of a catheter, steering the medical probe through a main vein or artery (typically, the femoral vein or artery), or, in the case of a surgical probe, advancing the medical probe through the surgical opening leading to the target site.

The physician then operates the medical probe to activate a functional component mounted at the probe distal end, thereby providing therapeutic treatment to and/or diagnosis of the interior region. Due to the potential of passing any of a variety of dangerous diseases from one patient to another, prudent consideration dictates that the re-use of such probes should be prevented or, at the least, minimized. Typically, medical probes that are re-used are sterilized between uses to kill any disease-causing agents and to remove any tissue that has collected on the medical probe during the previous use. Sterilization of used medical probes, however, is not fool-proof, and oftentimes ineffective when tissue located on the medical probe is not exposed to the full effect of the sterilization process. Thus, even a sterilized medical probe may pose a threat to patients.

Minimizing re-use of medical probes that provide therapy becomes even more critical. During the therapeutic process, it is important for the physician to control the therapeutic component at the probe distal end carefully and precisely, so that adverse damage to a therapeutic component of the medical probe does not occur. Sterilization of and re-use of therapeutic medical probes subjects the therapeutic component to mechanical, chemical and/or thermal stress, thus jeopardizing the control that the physician may have of the therapeutic component.

The need for careful and precise control over a therapeutic medical probe is especially critical during procedures that ablate tissue within the heart. These procedures, called electrophysiological therapy, are becoming more widespread for treating cardiac rhythm disturbances. When inside the desired chamber of the heart, the physician manipulates a steering mechanism to place one or more electrodes located at the distal end of the medical probe into direct contact with the heart tissue to be ablated. The physician then directs radio frequency energy from the electrodes through the tissue to an indifferent electrode, thereby ablating the tissue and forming a lesion. If the electrodes or the electrical wires connected thereto are worn or faulty, however, ablation may be ineffective and, in the worst case, may cause charring of the heart tissue.

Preventing or limiting re-usage of medical probes, while still allowing legitimate use of these probes, is made difficult by a possible scenario wherein the physician uses the medical probe, temporarily disconnects the probe from the control unit, and reconnects the probe to the control unit to continue the procedure. Thus, there is a danger of deeming the continued procedure to be re-usage of the medical probe, which may result in the probe being rendered prematurely inoperable.

Thus, it would be desirable to provide an improved medical system for minimizing the re-usage of medical probes, while still allowing legitimate use of these probes.

SUMMARY OF THE INVENTION

The present invention is directed to improved apparatus and methods for limiting the usage of medical probes, such as, e.g., catheters and surgical probes.

In a preferred method performed in accordance with a first aspect of the invention, usage of a medical probe having an electronic storage component for storing a probe identification code is limited by determining if the medical probe has been previously used and disabling the electronic storage component if the medical probe is determined to have been previously used. The probe identification code can be any indicator that identifies a particular aspect of the medical probe, such as, e.g., a serial number or a functional or physical characteristic of the medical probe. Disablement of the electronic storage component can be effected by any means that alters the output of the electronic storage component in a manner that indicates to a control unit, such as, e.g., an RF generator, that the medical probe should not be operated.

By way of non-limiting example, the electronic storage component can be disabled by modifying the probe identification code stored in the electronic storage component, such as, by clearing the probe identification code, or by modifying the functioning of the electronic storage component, such as by shorting the output of the electronic storage component. Determination of the previous usage of the medical probe is based on an elapsed time since an initial operation of the medical probe, and/or a number of times the medical probe has been operated, and/or a previous operation of the medical probe and a sterilization of the medical probe.

In an embodiment constructed in accordance with another aspect of the invention, a medical probe comprises an elongate member, an electronic storage component having stored therein a probe identification code, and disabling circuitry electrically coupled to the first electronic storage component, wherein the disabling circuitry is configured for detecting whether the medical probe has been previously used, and for disabling the electronic storage component if the medical probe is determined to have been previously used.

By way of non-limiting example, the electronic storage component comprises one or more resistors. The electronic storage component can, however, include any non-volatile component, such as, e.g., a microchip, that can store a probe identification code. The disabling circuitry can disable the electronic storage component by shorting the electronic storage component. The disabling circuitry detects whether the medical probe has been previously used by sensing disable signal that is transmitted thereto from an external source, such as, e.g., a control unit. Alternatively, the disabling circuitry can internally determine whether the medical probe has been previously operated by means, such as, e.g., detecting an elapsed time since an initial operation of the medical probe, and/or a number of times the medical probe has been operated, and/or a previous operation of the medical probe and a sterilization of the medical probe.

In another embodiment constructed in accordance with still a further aspect of the invention, a control unit for connection to a medical probe having an electronic storage component for storing a probe identification code, comprises control circuitry electrically coupled to the electronic storage component for determining if the medical probe has been previously used, and for disabling the electronic storage component if the medical probe is determined to have been previously used.

By way of non-limiting example, the control circuitry is a microprocessor and disables the electronic storage component by modifying the probe identification code stored in the electronic storage component, such as, by clearing the probe identification code, or by modifying the functioning of the electronic storage component, such as by shorting the output of the electronic storage component. Determination of the previous usage of the medical probe is based on an elapsed time since an initial operation of the medical probe, and/or a number of times the medical probe has been operated, and/or a previous operation of the medical probe and a sterilization of the medical probe. The control unit further comprises an RF power source, and an interlocking device electrically coupled between the RF power source and the microprocessor for preventing operation of the medical probe upon receipt of an interlocking control signal from the microprocessor.

In accordance with still a further aspect of the invention, a medical probe system comprises a medical probe carrying an electronic storage component storing a probe identification code, and a control circuit electrically coupled to the electronic storage component, wherein the control circuit is configured for determining if the medical probe has been previously used, and for disabling the electronic storage component if the medical probe is determined to have been previously used.

By way of non-limiting example, in a preferred embodiment of the medical probe system, the control circuit disables the electronic storage component by modifying the probe identification code by means, such as, e.g., clearing the probe identification code. The medical probe system further comprises disabling circuitry electrically coupled between the electronic storage component and the control circuit. The control circuit is configured for transmitting a disable signal to the disabling circuitry when the medical probe is determined to have been previously used, such disabling circuitry disables the electronic storage componentry, by means such as, e.g., modifying the functioning of the electronic storage componentry or modifying the probe identification code.

Other and further objects, features, aspects, and advantages of the present invention will become better understood with the following detailed description of the accompanying drawings.

BRIEF DESCRIPTION OF THE DRAWINGS

The drawings illustrate both the design and utility of preferred embodiments of the present invention, in which.

DETAILED DESCRIPTION OF THE PREFERRED EMBODIMENTS

Catheter System

Figure 1:
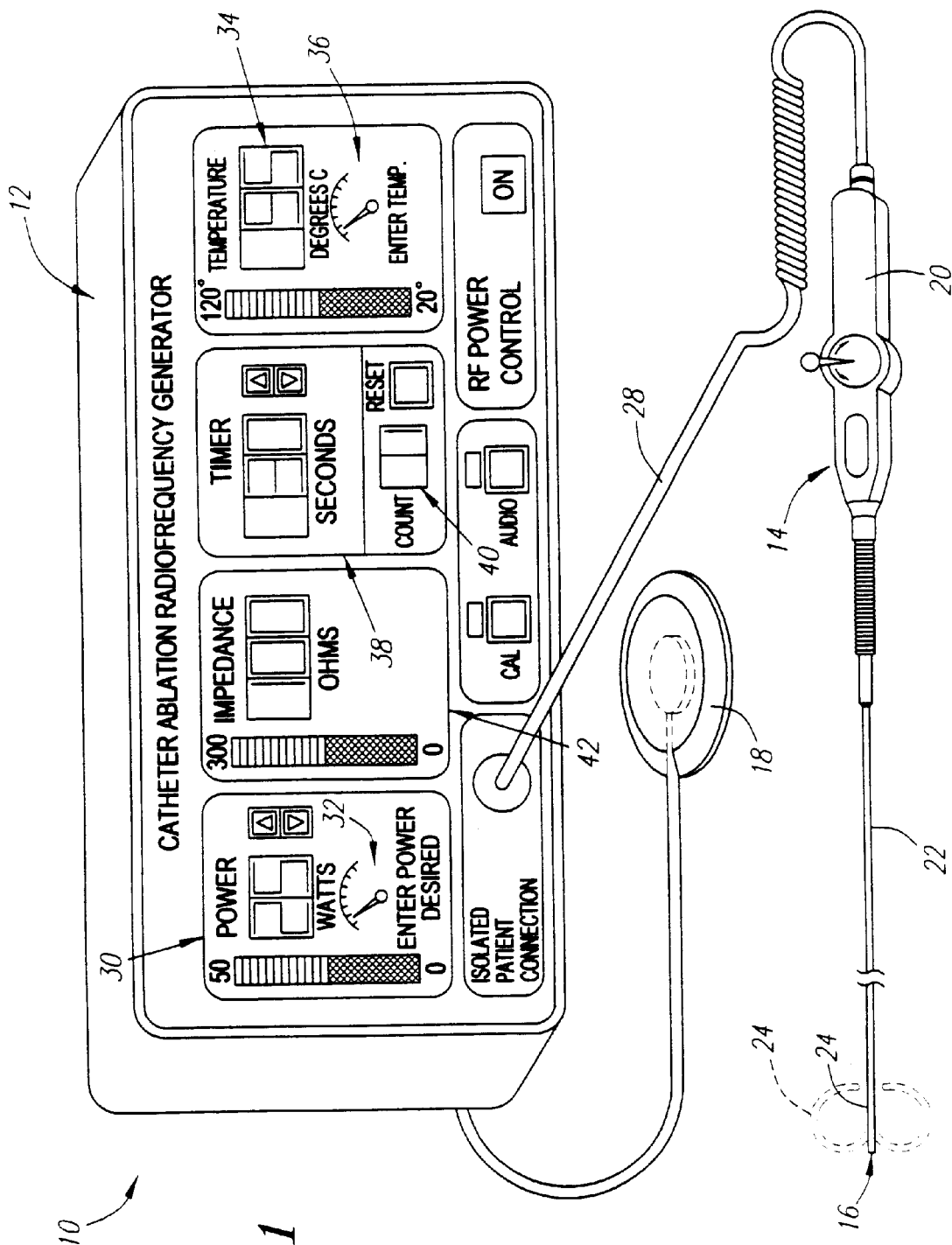
FIG. 1 is a perspective view of an embodiment of a catheter system in accordance with various aspects of the present invention.

FIG. 1 depicts a preferred embodiment of a catheter system 10 constructed in accordance with the present invention. The system 10 generally includes a radiofrequency generator 12, which delivers radio frequency energy, and a steerable catheter 14 carrying a radiofrequency emitting tip ablation electrode 16.

In the illustrated embodiment, the system 10 operates in a monopolar mode. In this arrangement, the system 10 includes a skin patch electrode that serves as an indifferent second electrode 18. In use, the indifferent electrode 18 is attached to the patient's back or other exterior skin area. Alternatively, the system 10 can be operated in a bipolar mode. In this mode, the catheter 14 carries both electrodes. In the illustrated embodiment, the ablation electrode 16 and the indifferent electrode 18 are made of platinum. The catheter 14 carries a temperature sensor 19 (shown in FIG. 2) adjacent the ablation electrode 16 to measure the temperature to which the tissue is exposed to during ablation.

The catheter 14 further includes a handle 20, a guide tube 22, and a tip 24, which carries the ablation electrode 16. The handle 20 encloses a steering mechanism 26 for the catheter tip 24. A cable 28 extending from the rear of the handle 20 has plugs (not shown). The plugs connect the catheter 14 to the generator 12 for conveying radiofrequency energy to the ablation electrode 16. The radiofrequency energy heats the tissue to form the lesion.

Left and right steering wires (not shown) extend through the guide tube 22 to interconnect the steering mechanism 26 to the left and right sides of the tip 24. Rotating the steering mechanism 26 to the left pulls on the left steering wire, causing the tip 24 to bend to the left. Also, rotating the steering mechanism 26 to the right pulls on the right steering wire, causing the tip 24 to bend to the right. In this way, the physician steers the ablation electrode 16 into contact with the tissue to be ablated.

Upon initial power on, the generator 12 is placed in a standby mode, which allows the physician to adjust the setpoint parameters. These setpoint parameters include the magnitude of the RF power delivered, tissue temperature and duration of RF power delivery.

The RF power delivered by the generator 12 is set using a power control input 30. The actual RF power delivered by the generator 12 is reported by a power meter 32. During RF energy delivery, the generator 12 adjusts power output to maintain an actual measured temperature at the temperature setpoint. Thus, the measured power may be lower than the setpoint power depending on the measured tissue temperature and/or tissue impedance.

The desired temperature to which the ablated tissue is exposed is set using a temperature control input 34. The actual temperature to which the ablated tissue is exposed is reported by a temperature gauge 36. The desired duration of RF power application is set using a timer 38. A counter 40 tracks the elapsed time from initial delivery of RF power to the tissue, and counts from zero to the setpoint duration. When loss of contact with tissue is detected; the counter 40 stops. Contact between the ablation electrode 16 and the tissue is measured with an impedance meter 42.

The generator 12 includes an RF power control button 44, the depression of which places the generator 12 in deliver mode. While in the deliver mode, the generator 12 delivers RF energy to the tissue in contact with the ablation electrode 16 until the count displayed by the counter 40 reaches the setpoint duration or until the RF power control button 44 is depressed again.

Medical Probe System

Figure 12:
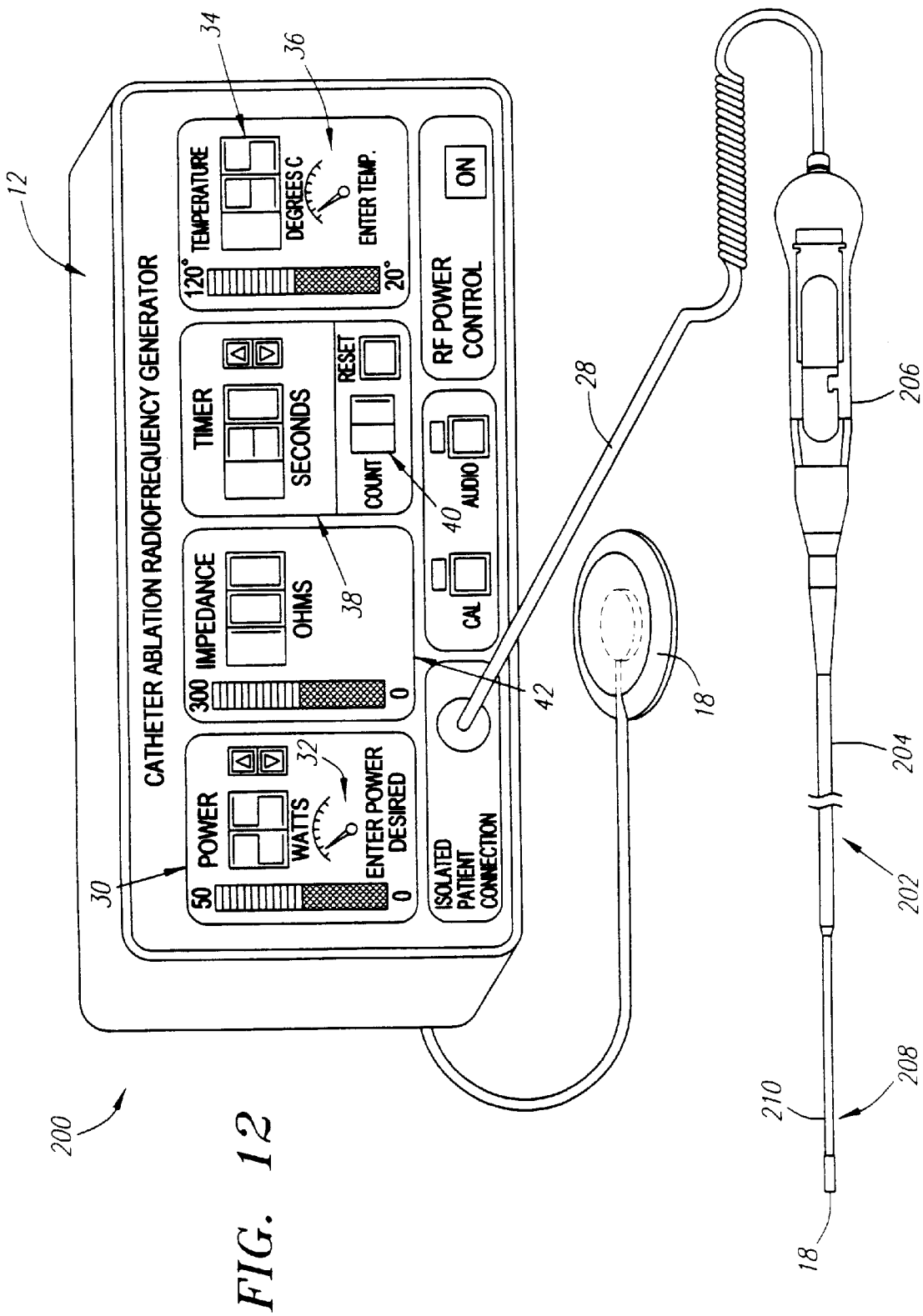
FIG. 12 is a perspective view of an embodiment of a surgical probe system in accordance with various aspects of the present invention.

FIG. 12 depicts a preferred embodiment of a surgical probe system 200 constructed in accordance with the present invention. The surgical probe system 200 is similar to the catheter system 10 described above. Accordingly, elements of the surgical probe system 200 that are similar to those of the catheter system 10 have been given common reference numbers. Like the catheter system 10, the system 200 includes a radiofrequency generator 12, the details of which are described above. The system 200 further includes a surgical probe 202 that includes a relatively short, relatively stiff shaft 204, a handle 206, and a distal section 208. The shaft 204 may be from about 4 inches to 18 inches in length and is preferably about 6 to 8 inches. The distal section 208 may be from about 1 inch to 10 inches in length and is preferably about 4 to 6 inches. The shaft 204 supports a radiofrequency emitting tip ablation electrode 16, much like that described above, and a plurality of coil electrodes 210. This embodiment is particularly useful because it can be easily inserted into the patient through an introducing port such as a trocar.

Additional information concerning the above-described and other surgical probes may be found in U.S. application Ser. No. 09/072,872, filed May 5, 1998, entitled "Surgical Method and Apparatus for Positioning a Diagnostic or Therapeutic Element Within the Body," which is incorporated herein by reference.

Interaction between the surgical probe 202 and the RF generator 12 is similar to that described above between the catheter 14 and the RF generator 12. For purposes of brevity, such operation will not be repeated.

Figure 2:
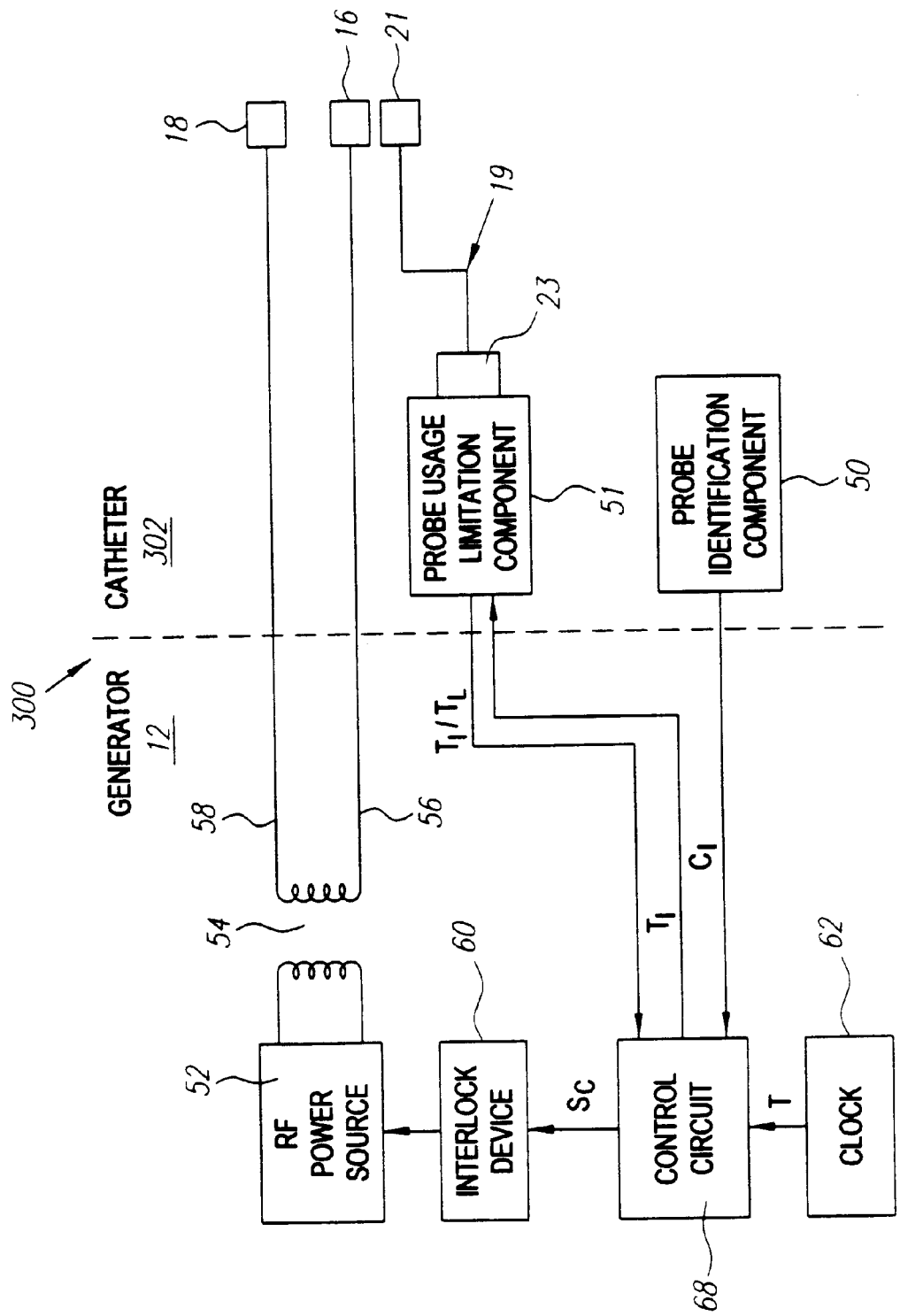
FIG. 2 is a schematic of a preferred embodiment of a medical probe system.

Referring to FIG. 2, a medical probe system 300, which can take the form of the catheter system 10 or surgical probe system 200 described above, is depicted. A medical probe 302 (i.e., the catheter 14 or surgical probe 202) includes a probe identification component 50, which is capable of storing a probe identification code $C_I$. The probe identification code $C_I$ uniquely identifies the medical probe 302, such as by a serial number, or uniquely identifies a characteristic of the medical probe 302, such as, e.g., a particular performance and/or physical characteristic of the medical probe 302. In the illustrated embodiment, the probe identification component 50 is a non-volatile storage component, and particularly is a non-solid state device, such as, e.g., one or more resistors, the resistance value of which represents the probe identification code $C_I$. Alternatively, the probe identification component 50 is a microchip, such as, e.g., a ROM, which has been preprogrammed with a digital identification code $C_I$.

The medical probe 302 further includes a probe usage limitation component 51. In this embodiment, the probe usage limitation component 51 is a non-volatile electronic storage component that is capable of storing data. Of course, the entire data need not be stored in a single component, but may be stored in several components without straying from the principles taught by this invention. For purposes of illustration, the probe identification component 50 and the probe usage limitation component 51 are depicted as separate components. It should be noted, however, that the functions performed by the probe identification component 50 and the probe usage limitation component 51 can, in most instances, be performed within a single component.

Limiting Re-Use of Devices Based on Time Elapsed from First Use

The medical probe system 300 is capable of identifying and disabling re-used single use devices based on the time elapsed from the first therapeutic use of the medical probe 302. In this regard, the probe usage limitation component 51 is able to store an initial probe usage time $T_I$ and a predetermined elapsed time limit $T_L$. The initial probe usage time $T_I$ is written into the probe usage limitation component 51 by the generator 12 when the medical probe 302 is initially operated. Subsequently, the initial probe usage time $T_I$ can be read from the probe usage limitation component 51 and used to limit re-usage of the medical probe 302, based on the initial operation of the medical probe 302.

Utility of storing the initial probe usage time $T_I$ within the probe usage limitation component 51, however, is not to be limited to limiting re-usage of the medical probe 302, but may extend to any application wherein knowledge of the time of the initial operation of the medical probe 302 would be useful. For example, the initial probe usage time $T_I$ can be read from a faulty medical probe to facilitate troubleshooting of the medical probe.

The predetermined elapsed time limit $T_L$ is written into the probe usage limitation component 51, preferably during the manufacturing process. The predetermined elapsed time limit $T_L$ represents the amount of time after the medical probe has been initially operated that the medical probe remains operable. Preferably, the value of the predetermined elapsed time limit $T_L$ is selected to minimize re-use of the medical probe 302, while still allowing legitimate use of the medical probe 302. For example, the value of the predetermined elapsed time limit $T_L$ can be selected to be between the maximum time expected to perform a therapeutic ablation procedure on a patient and the minimum time expected to complete a sterilization cycle on the medical probe 302. By way of non-limiting example, the value of the predetermined elapsed time limit $T_L$ can be selected to be 24 hours.

In the illustrated embodiment, the probe usage limitation component 51 comprises an EEPROM. Preferably, the probe usage limitation component 51 includes temperature-sensing capability to provide a known reference temperature $T_I$ for the temperature sensor 19, which, in the illustrated embodiment, is a thermocouple having a first temperature-sensing element 21 located adjacent the ablation electrode 16, and a second temperature-sensing element 23 located in the handle 20 (shown in FIG. 1) adjacent the probe usage limitation component 51. In this manner, the need for a thermistor, which was previously used to measure the reference temperature adjacent the second temperature-sensing element 23, is obviated. By way of non-limiting example, a Model DS2434 battery identification chip manufactured by Dallas Semiconductor is an EEPROM that provides temperature-sensing capability.

The structure of the probe usage limitation component 51 is not limited to an EEPROM, but can take the form of any non-volatile component that allows storage of data therein on-the-fly. Alternatively, the structure of the probe usage limitation component 51 can comprise other microchips, such as, e.g., non-volatile RAM or volatile RAM in conjunction with a battery.

The generator 12 includes an RF power source 52, which is connected through a transformer 54 to first and second conducting lines 56 and 58. In the illustrated environment, the power source 52 delivers up to 150 watts of power at a frequency of 500 kHz. The first conducting line 56 leads to the ablation electrode 16, and the second conducting line 58 leads to the indifferent electrode 18. The generator 12 further includes an interlock device 60, which is electrically coupled to the power source 52. Activation of the interlock device 60 via a control signal prevents the power source 52 from outputting power to the transformer 54, thereby preventing delivery of RF energy to the tissue to be ablated.

The generator 12 includes a clock 62, which, as will be discussed in further detail below, generates a time signal T for time-keeping functions. In the illustrated embodiment, the time signal T represents an absolute time, such as, e.g., what one may obtain from a standard household clock.

The generator 12 further includes a control circuit 68, which is electrically coupled to the clock 62 to obtain the time signal T. The control circuit 68 is electrically coupled to the probe usage limitation component 51 of the medical probe 302 when the medical probe 302 is physically connected to the generator 12, so that the control circuit 68 can read and write data to and from the probe usage limitation component 51.

The control circuit 68 is configured for deriving an initial probe usage time $T_I$ from the time signal T when the medical probe is initially operated, and for writing the initial probe usage time $T_I$ to the probe usage limitation component 51, assuming that the probe usage limitation component 51 has not previously been initialized with the initial probe usage time $T_I$. In this manner, the initial probe usage time $T_I$ is reported to the generator 12 or a like generator if the medical probe 302 is reconnected to the generator 12, i.e., when the medical probe 302 is physically disconnected from the generator 12 and then physically reconnected to the generator 12 or like generator.

The control circuit 68 is further configured for reading the initial probe usage time $T_I$ from the probe usage limitation component 51, and generating an interlock control signal $S_C$ based on the initial probe usage time $T_I$. In particular, the control circuit 68 is configured for reading the predetermined elapsed time limit $T_L$ from the probe usage limitation component 51 and determining if the predetermined elapsed time limit $T_L$ has expired. The control circuit 68 determines expiration of the predetermined elapsed time limit $T_L$ by determining an elapsed probe usage time $T_E$ based on a comparison between initial probe usage time $T_I$ and a reference time $T_R$ obtained from the time signal T, i.e., the initial probe usage time $T_I$ is subtracted from the reference time $T_R$. In the illustrated embodiment, the reference time $T_R$ represents the current absolute time. The control circuit 68 then compares the elapsed probe usage time $T_E$ with the predetermined elapsed time limit $T_L$ to determine if the predetermined elapsed time limit $T_L$ has expired, i.e., if the elapsed probe usage time $T_E$ exceeds the predetermined elapsed time limit $T_L$, the predetermined elapsed time limit $T_L$ is considered expired. For the purposes of this invention, the value of the elapsed probe usage time $T_E$ exceeds the value of the predetermined elapsed time limit $T_L$ if the value of the elapsed probe usage time $T_E$ is equal to or greater than the value of the predetermined elapsed time limit $T_L$.

The control circuit 68 is electrically coupled to the interlock device 60 and applies the interlock control signal $S_C$ thereto. Application of the interlock control signal $S_C$ activates the interlock device 60, preventing power from being outputted from the power source 52, and in turn, preventing subsequent conveyance of RF energy to tissue in contact with the ablation electrode 16.

Figure 3:
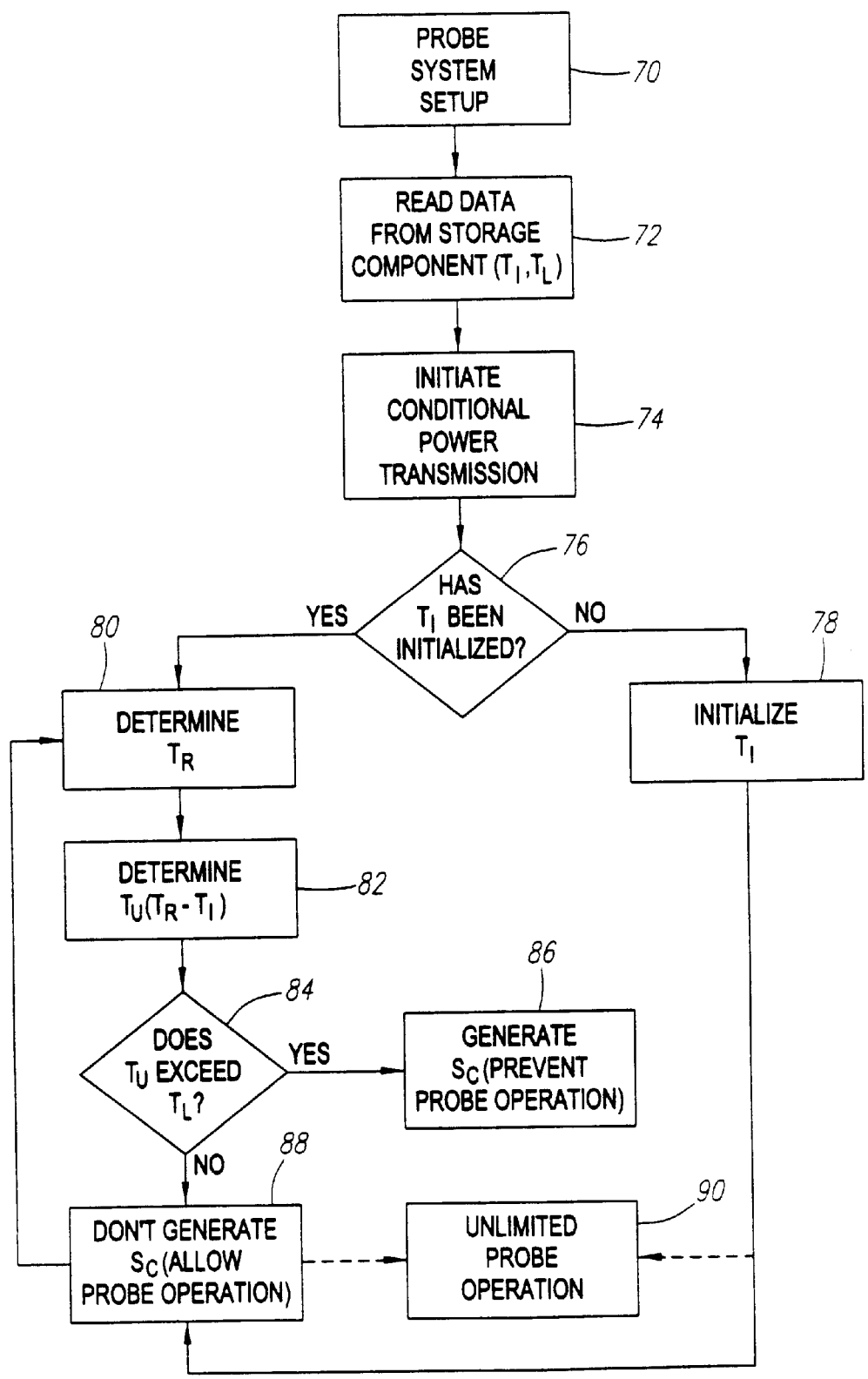
FIG. 3 is a flow diagram of a preferred method of conditionally operating a medical probe employed in the medical probe system of FIG. 2.

With reference to FIG. 3, operation of the medical probe system 300, in identifying and disabling re-used single use devices based on the time elapsed from the first therapeutic use of the medical probe 302, will now be described. Without knowledge of whether the medical probe 302 has been previously operated, the medical probe system 300 is set up by physically connecting the medical probe 302 to the generator 12 and powering on the generator 12 (step 70). At this point, the generator 12 is in standby mode. The generator 12 then reads the data from the probe usage limitation component 51 (step 72). After insertion of the medical probe 302 within the patient's body and placement of the ablation electrode 16 in contact with the tissue to be ablated, the RF power control button 44 is depressed to conditionally initiate power transmission from the generator 12 and subsequent delivery of RF energy to the tissue (step 74). At this point, the generator 12 is in delivery mode.

The generator 12 then determines whether the probe usage limitation component 51 has already been initiated with an initial probe usage time $T_I$ by analyzing the data read from the probe usage limitation component 51 (step 76). If the probe usage limitation component 51 has not already been initialized with the initial probe usage time $T_I$, the generator 12 initializes the probe usage limitation component 51 with the initial probe usage time $T_I$ (step 78). That is, the generator 12 derives the initial probe usage time $T_I$ from the timing signal T, and writes the initial probe usage time $T_I$ into the probe usage limitation component 51 of the medical probe 302. In this manner, if the medical probe 302 is physically disconnected and reconnected to the generator 12 or like generator and conditionally operated, the generator 12 or like generator can ascertain when the medical probe 302 was initially operated. Since the medical probe 302 has not been previously operated, the generator 12 then allows operation of the medical probe 302, i.e., the interlock control signal $S_C$ is not generated (step 88).

In the illustrated embodiment, initialization of the probe usage limitation component 51 occurs upon effective operation of the medical probe 302, i.e., operation of the medical probe 302 in such a manner as to form a lesion on the tissue. In this regard, to prevent premature initiation of the probe usage limitation component 51, the generator 12 does not write to the probe usage limitation component 51 during non-therapeutic operation of the medical probe 302, i.e., when operation of the medical probe 302 does not result in a tissue lesion. Such probe operation can be caused by a variety of reasons, including inadequate contact between the ablation electrode 16 and the tissue, inadequate energy delivery to the ablation electrode 16 and inadequate duration of energy application.

After initiation of the probe usage limitation component 51 with the initial probe usage time $T_I$ (step 78), or if the generator 12 determines that the probe usage limitation component 51 has already been initialized with the initial probe usage time $T_I$ (step 76), the generator 12 determines whether the predetermined elapsed time limit $T_L$ has expired (steps 80–84). First, the reference time $T_R$ is determined from the time signal T (step 80). Then, the elapsed probe usage time $T_E$ is determined by subtracting the initial probe usage time $T_I$ from the reference time $T_R$ (step 82). Then, the elapsed probe usage time $T_E$ is compared to the predetermined elapsed time limit $T_L$ (step 84).

If the elapsed probe usage time $T_E$ exceeds the predetermined elapsed time limit $T_L$, the generator 12 prevents operation of the medical probe 302, i.e., the interlock control signal $S_C$ is generated, which is subsequently transmitted to the interlock device 60 (step 86). The medical probe 302 is thus rendered inoperable and cannot be re-used, thereby preventing further operation of the medical probe 302. If the value of the elapsed probe usage time $T_E$ does not exceed the value of the predetermined elapsed time limit $T_L$, the generator 12 allows operation of the medical probe 302, i.e., the interlock control signal $S_C$ is not generated (step 88).

The generator 12 periodically (e.g., every second) determines if the elapsed probe usage time $T_E$ has expired and conditionally allows operation of the medical probe 302, based on the expiration of the elapsed probe usage time $T_E$, until the medical probe 302 is disconnected from the generator 12 (steps 80–88). Alternatively, the expiration of the elapsed probe usage time $T_E$ is determined only one time per probe connection. That is, once the elapsed probe usage time $T_E$ is determined not to be expired, the medical probe 302 can be operated without limitation until the medical probe 302 is physically disconnected from, and again connected, to the generator 12 (step 90).

In this manner, the physician has a certain amount of time in which to operate the medical probe 302 after initiation of the probe usage limitation component 51, notwithstanding the fact that the medical probe 302 can be repeatedly disconnected from and reconnected to the generator 12. Thus, re-usage of the medical probe 302 can be minimized without prematurely rendering the medical probe 302 inoperable.

Limiting Re-Use of Devices Based On Detecting Environment Changes

Figure 4:
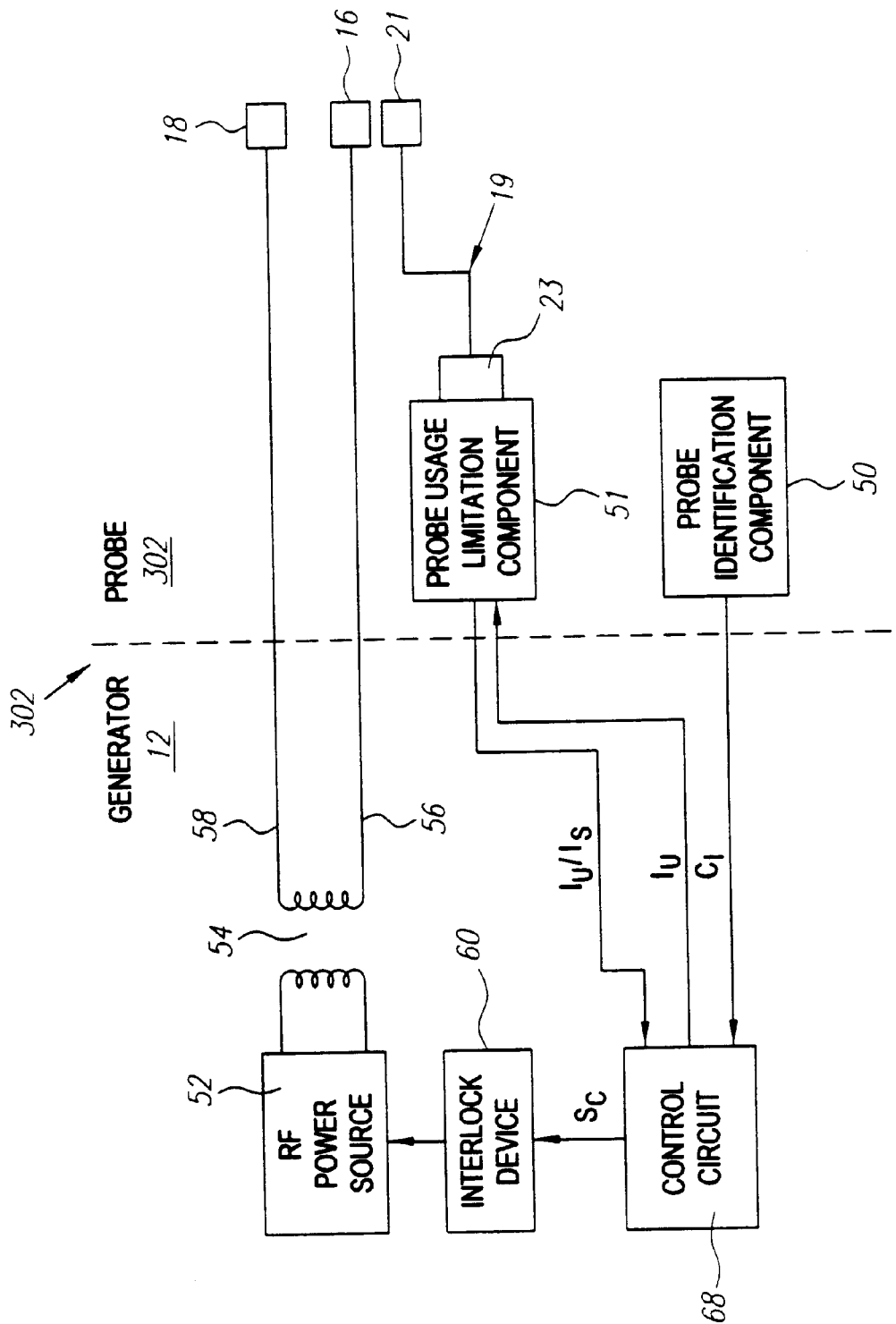
FIG. 4 is a schematic of an alternative preferred embodiment of a medical probe system.

Referring to FIG. 4, the medical probe system 300 is capable of identifying and disabling re-used single use devices based on detecting environmental changes. In this regard, the probe usage limitation component 51 is capable of detecting an environmental condition to which the medical probe 302 is exposed, and determines if the environmental condition is indicative of exposure of the medical probe 302 to a sterilization cycle.

In a typical sterilization procedure, the medical probe 302 is placed inside a breathable pouch, and a biological indicator is applied to the medical probe 302 according to a validated hospital procedure. The medical probe 302 and pouch are then placed inside a sterilization chamber and exposed to a sterilization cycle. The sterilization cycle may, for example, include preconditioning, exposure, post-vacuum, and aeration steps, which are performed under a variety of environmental conditions. For example, the preconditioning step may involve subjecting the medical probe 302 to a temperature of 125–145° F., humidity of 55–75%, and a pressure (vacuum) at 1.9–3.9 p.s.i.a. for 30–45 minutes. The exposure step may involve subjecting the medical probe 302 to an oxide, such as, e.g., 100% ethylene oxide (EO) at 600 mg/L, and a temperature of 125–145° F. for four hours. The post-vacuum step may involve twice subjecting the medical probe 302 to a pressure (vacuum) of 1.9–3.9 p.s.i.a. The aeration step may involve subjecting the medical probe 302 to a temperature of 120° F.–145° F. for twelve hours.

Thus, if the probe usage limitation component 51 detects an environmental condition that is indicative of a sterilization cycle, such as, e.g., temperature, humidity, pressure or chemical, then the probe usage limitation component 51 stores a probe sterilization indicator $I_S$ indicating that the medical probe 302 has been sterilized. For example, if the probe usage limitation component 51 detects one or more of the following conditions: a temperature above 125° F., a humidity above 55%, a pressure below 3.9 p.s.i.a., or an oxide, such as, e.g., EO, the probe usage limitation component 51 stores a probe sterilization indicator $I_S$.

Preferably, as part of the post-manufacturing process, the medical probe 302 is subjected to an initial sterilization cycle. In this case, the medical probe 302 will be shipped to the physician with the probe sterilization indicator $I_S$ stored in the probe usage limitation component 51. The control circuit ultimately limits re-usage of the medical probe 302, based on a detection of a re-sterilization of the medical probe 302, an indication that the physician is attempting to operate the medical probe 302 illegitimately. A medical probe 302 that has been re-sterilized (the operation of which would be considered illegitimate operation of the medical probe 302) must be distinguished from a medical probe 302 that has been sterilized only once as a part of the post-manufacture process (the operation of which would be considered legitimate). In this regard, as will be discussed in further detail below, the probe usage limitation component 51 is configured for storing a previous probe usage indicator $I_U$, indicating that the medical probe 302 has been previously operated and allowing post-manufacturing sterilization to be distinguished from re-sterilization of the medical probe 302.

In the illustrated embodiment, the probe usage limitation component 51 comprises battery-operated non-volatile RAM with environmental sensing capabilities. A non-limiting example of such a probe usage limitation component 51 is an electrolytic sensor or chemFET.

The control circuit 68 is configured for reading data from the probe usage limitation component 51 and determining if the data comprises the probe sterilization indicator $I_S$ and the previous probe usage indicator $I_U$, and generating an interlock control signal $S_C$ based on the presence of the probe sterilization indicator $I_S$ and the previous probe usage indicator $I_U$ within the data read from the probe usage limitation component 51. In particular, the interlock control signal $S_C$ is generated if both the probe sterilization indicator $I_S$ and the previous probe usage indicator $I_U$ are present, or if both the probe sterilization indicator $I_S$ and the previous probe usage indicator $I_U$ are not present. The interlock control signal $S_C$ is not generated if the probe sterilization indicator $I_S$ is present and the previous probe usage indicator $I_U$ is not present, or if the probe sterilization indicator $I_S$ is not present and the previous probe usage indicator $I_U$ is present.

Figure 5:
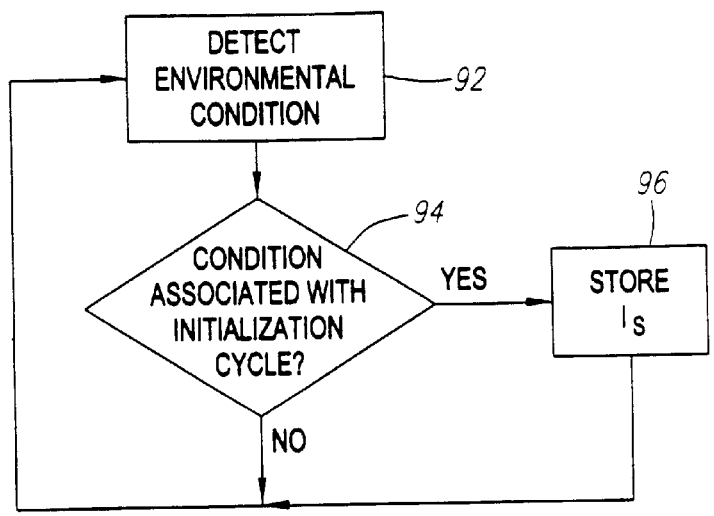
FIG. 5 is a flow diagram of a preferred method of storing a probe sterilization indicator within a medical probe employed in the medical probe system of FIG. 4.

With reference to FIG. 5, operation of the medical probe 302 during sterilization will now be described. After manufacture of the medical probe 302, the probe usage limitation component 51 carried by the medical probe 302 is continuously detecting an environmental condition to which the medical probe 302 is exposed (step 92). The environmental condition detected by the probe usage limitation component 51 can be, e.g., temperature, pressure, moisture and/or chemical-based. The probe usage limitation component 51 then determines if the environmental condition detected is associated with a sterilization cycle, i.e., if the environmental condition matches a known environmental condition to which probes are subjected during the sterilization cycle (step 94). If the probe usage limitation component 51 detects an environmental condition associated with the sterilization cycle, such as, e.g., a temperature of 130° F., the probe usage limitation component 51 stores the probe sterilization indicator $I_S$, indicating that the medical probe 302 has been either sterilized, whether it be legitimately during the post-manufacture process or illegitimately during a re-sterilization process (step 96). This sterilization indicator $I_S$ is reported later to the generator 12 to indicate that the medical probe 302 has been sterilized. The probe usage limitation component 51 continuously detects and determines if the environmental condition to which the medical probe 302 is exposed is associated with a sterilization cycle.

Figure 6:
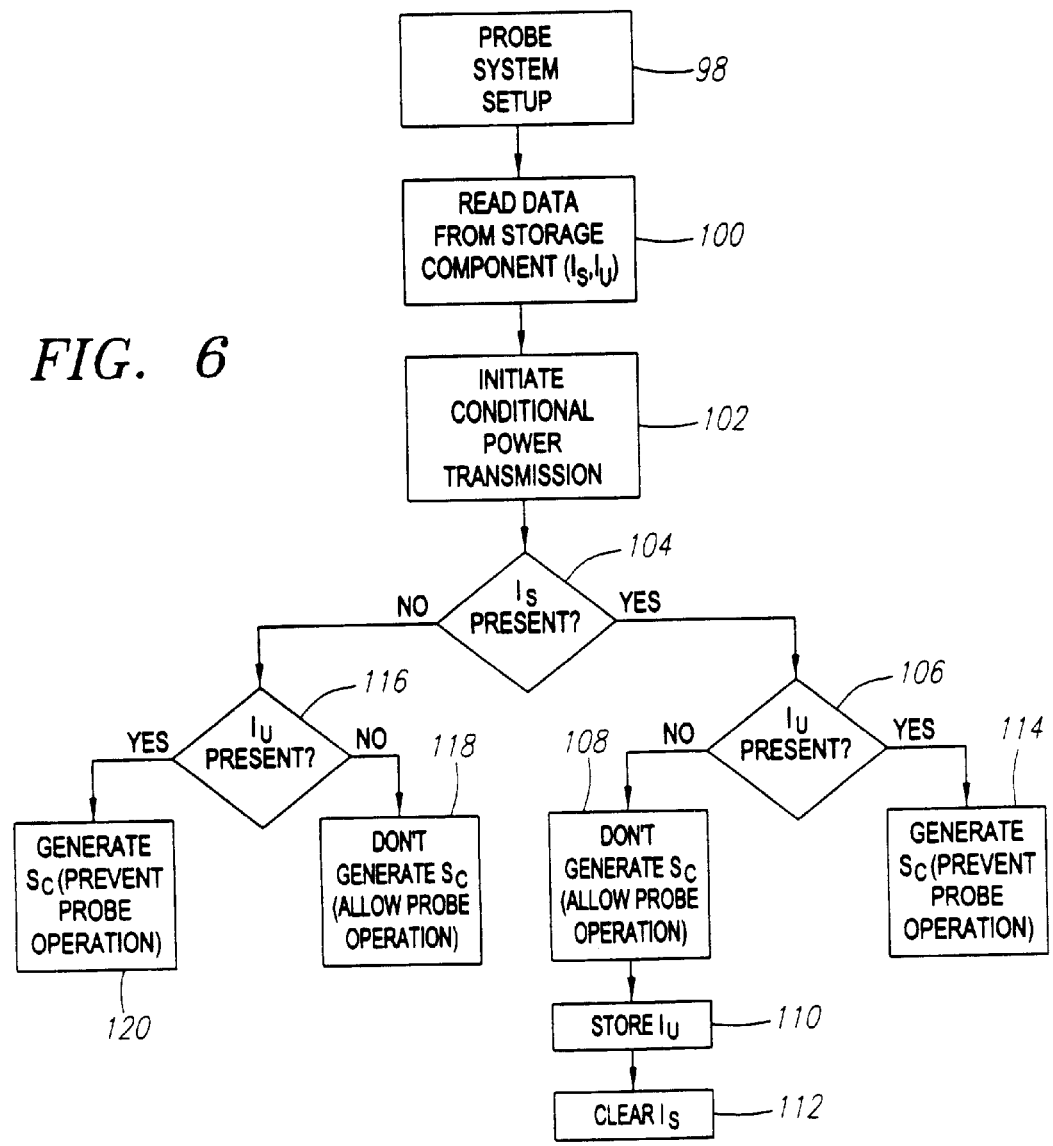
FIG. 6 is a flow diagram of a preferred method of conditionally operating a medical probe employed in the medical probe system of FIG. 4.

With reference to FIG. 6, operation of the medical probe system 300, in identifying and disabling re-used single use devices based on detecting environmental changes, will now be described. Without knowledge of whether the medical probe 302 has been sterilized or previously operated, the medical probe system 300 is set up by physically connecting the medical probe 302 to the generator 12 and powering on the generator 12 (step 98). At this point, the generator 12 is in standby mode. The generator 12 then reads the data from the probe usage limitation component 51 (step 100). After insertion of the medical probe 302 within the patient's body and placement of the ablation electrode 16 in contact with the tissue to be ablated, the RF power control button 44 (shown in FIG. 1) is depressed to conditionally initiate power transmission from the generator 12 and subsequent delivery of RF energy to the tissue (step 102). At this point, the generator 12 is in delivery mode.

The generator 12 then determines whether the probe sterilization indicator $I_S$ is present in or absent from the data read from the probe usage limitation component 51, and thus whether the medical probe 302 has been sterilized (step 104). If the probe sterilization indicator $I_S$ is present, the generator 12 determines whether the previous probe usage indicator $I_U$ is present in the data read from the probe usage limitation component 51, and thus whether the medical probe 302 has been previously operated (step 106). If the previous probe usage indicator $I_U$ is absent, the medical probe 302 is determined to be sterilized and unused. Thus, the generator 12 allows operation of the medical probe 302, i.e., the interlock control signal $S_C$ is not generated (step 108).

The generator 12 then writes the previous probe usage indicator $I_U$ to the probe usage limitation component 51 (step 110). In this manner, if the medical probe 302 is physically disconnected and reconnected to the generator 12 or like generator and conditionally operated, either legitimately or illegitimately, the generator 12 or like generator can ascertain that the medical probe 302 has been previously operated. The generator 12 also clears the probe sterilization indicator $I_S$ from the probe usage limitation component 51 (step 112). In this manner, if the medical probe 302 is physically disconnected and reconnected to the generator 12 without undergoing a sterilization cycle, the medical probe 302 will not be prematurely rendered inoperable, which would otherwise result from the presence of the previous probe usage indicator $I_U$. That is, as will be discussed in further detail below, if the probe sterilization indicator $I_S$ is absent and the previous probe usage indicator $I_U$ is present, the medical probe 302 can still be operated.

In the illustrated embodiment, storage of the previous probe usage indicator $I_U$ into the probe usage limitation component 51 occurs upon effective operation of the medical probe 302, i.e., operation of the medical probe 302 in such a manner as to form a lesion on the tissue. In this regard, to prevent premature storage of the previous probe usage indicator $I_U$ into the probe usage limitation component 51, the generator 12 does not write to the probe usage limitation component 51 during non-therapeutic operation of the medical probe 302, i.e., when faulty operation of the medical probe 302 does not result in a tissue lesion. Such faulty probe operation can be caused by a variety of reasons including, inadequate contact between the ablation electrode 16 and the tissue, inadequate energy delivery to the ablation electrode 16 and inadequate duration of energy application.

If the previous probe usage indicator $I_U$ is present (step 106), the medical probe 302 is determined to have been previously used and re-sterilized illegitimately, and thus, the generator 12 prevents operation of the medical probe 302, i.e., the interlock control signal $S_C$ is generated (step 114).

If the probe sterilization indicator $I_S$ is absent (step 104), the generator 12 determines if the previous probe usage indicator $I_U$ is present in, or absent from, the data read from the probe usage limitation component 51 (step 116). If the previous probe usage indicator $I_U$ is present, the medical probe 302 is determined to have been physically disconnected from, and reconnected to, the generator 12 in the middle of a procedure, and thus further operation of the medical probe 302 is legitimate. As such, the generator 12 allows operation of the medical probe 302, i.e., the interlock control signal $S_C$ is not generated (step 118).

If, after the probe sterilization indicator $I_S$ is determined to be absent, the previous probe usage indicator $I_U$ is absent, the medical probe 302 is determined to be improperly initially sterilized or not sterilized at all, and thus, the generator 12 prevents operation of the medical probe 302, i.e., the interlock control signal $S_C$ is generated (step 120).

In this manner, as long as the medical probe 302 is not re-sterilized, the physician can operate the medical probe 302 after initiation of the probe usage limitation component 51, notwithstanding the fact that the medical probe 302 can be repeatedly disconnected from and reconnected to the generator 12. Thus, re-usage of the medical probe 302 can be minimized without prematurely rendering the medical probe 302 inoperable.

The medical probe system 300 can use other probe indicators in combination with the probe sterilization indicator $I_S$ to identify and disable re-used single use devices based on detecting environmental changes. For example, when the medical probe 302 is manufactured, the estimated sterilization date of the medical probe 302, or alternatively, the manufacture date of the medical probe 302, can be stored in the probe usage limitation component 51. A typical estimated probe sterilization date is a month after the manufacture date of the probe. Upon actual sterilization of the medical probe 302, the probe sterilization indicator $I_S$ and the date of actual sterilization are stored in the probe usage limitation component 51. Upon connection of the medical probe 302 to the RF generator 12, if the probe sterilization indicator $I_S$ is absent, the medical probe 302 is determined to be un-sterilized, and therefore is prevented from being operated. If the sterilization indicator $I_S$ is present and the actual date of sterilization is later the estimated actual date of sterilization, the medical probe 302 is determined to be re-sterilized, and therefore is prevented from being operating.

The probe sterilization indicator $I_S$ cannot only be used to limit re-usage of medical probes 302, but can also be used to enforce the shelf-life of medical probes 302. In this regard, upon sterilization of the medical probe 302, the sterilization indicator $I_S$ and actual date of sterilization can be stored in the probe usage limitation component 51. If, upon connection of the medical probe 302 to the RF generator 12, the difference between the actual sterilization date and the current date exceeds a predetermined period of time (i.e., the shelf-life of the medical probe 302), the medical probe 302 is prevented from being operated.

Limiting Re-Use of Devices Based on Cataloging Catheter Usage

Figure 7:
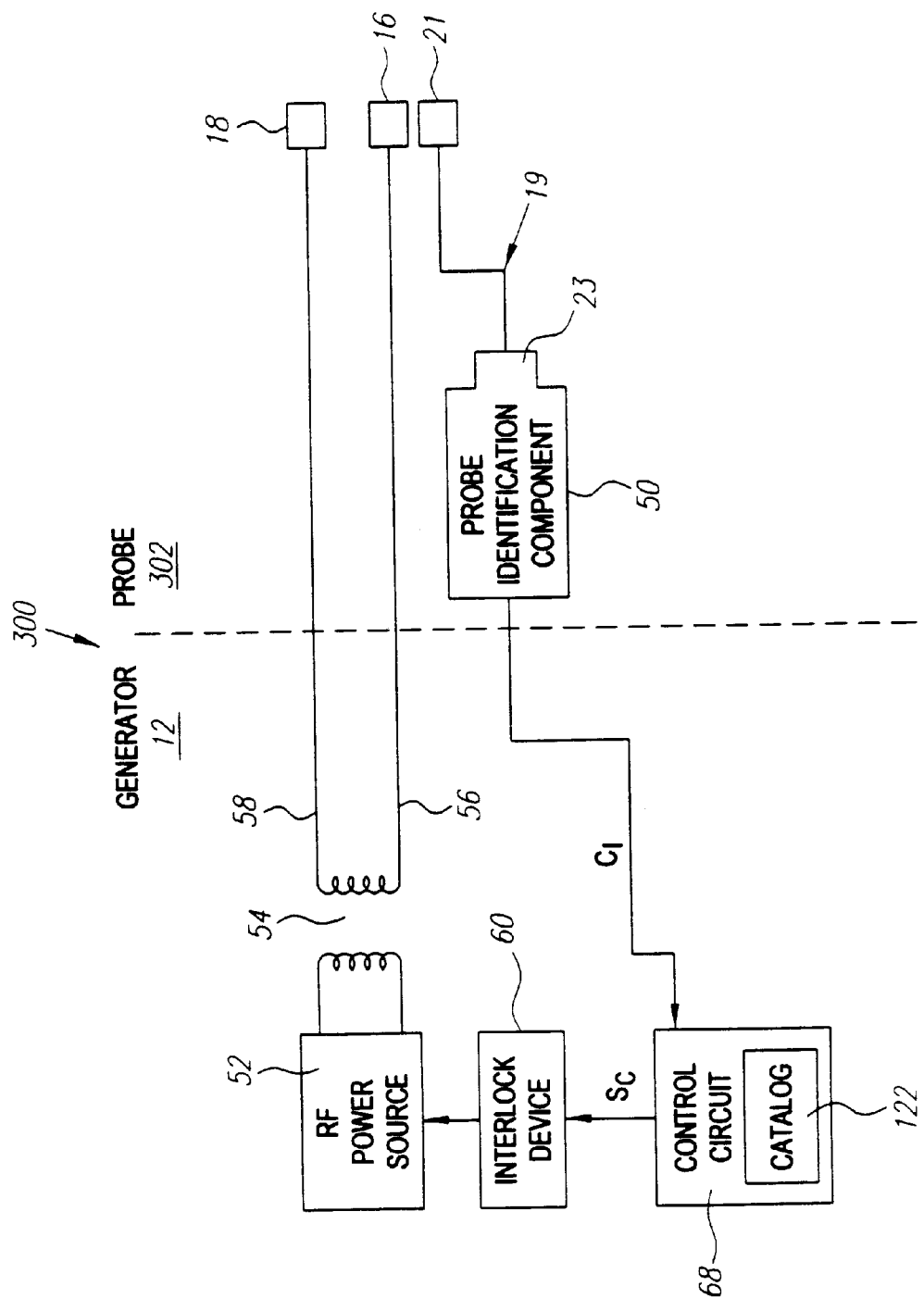
FIG. 7 is a schematic of another alternative preferred embodiment of a medical probe system.
Figure 8:
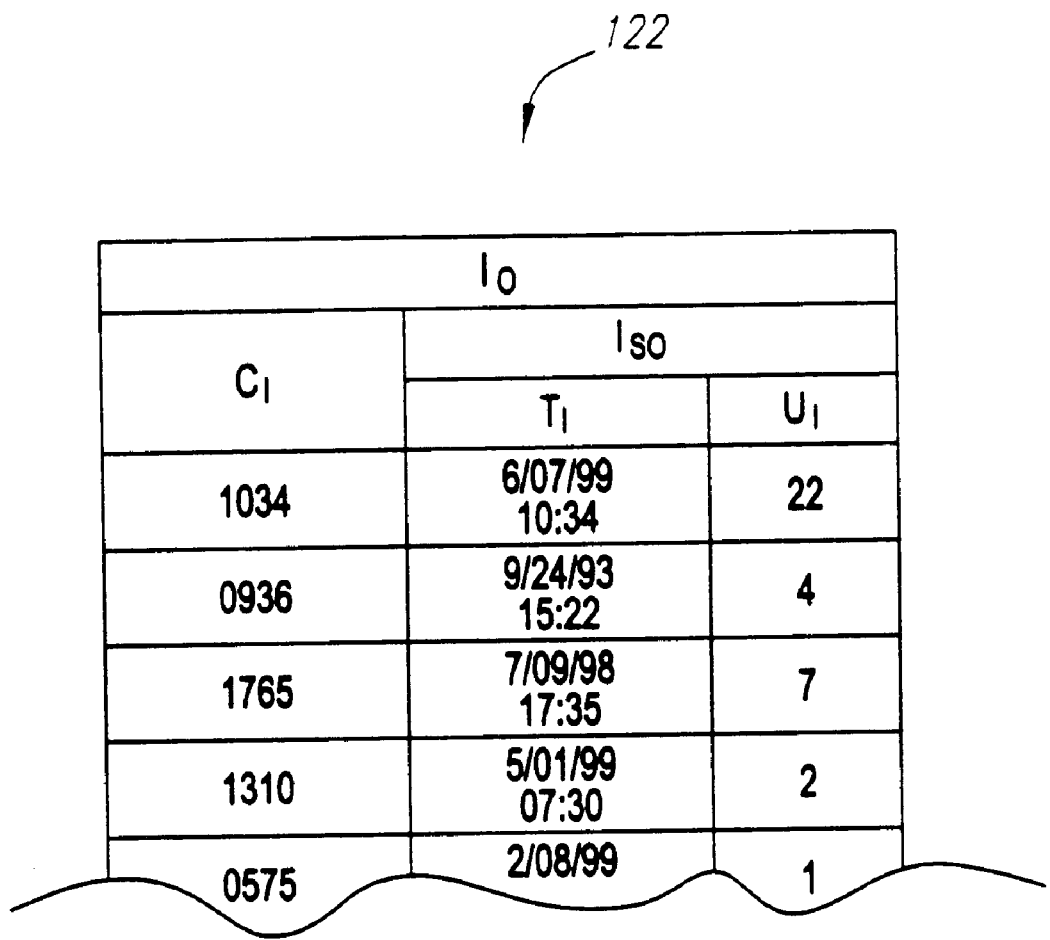
FIG. 8 is a schematic of a catalog employed in the medical probe system of FIG. 7.

Referring to FIGS. 7 and 8, the medical probe system 300 is alternatively capable of identifying and disabling re-used single use devices based on cataloging catheter usage. In this regard, the control circuit 68 includes a catalog 122 (shown in further detail in FIG. 8), obviating the need for a probe usage limitation component 51 within the medical probe. In this embodiment, the control circuit 68 is configured for storing historical operational indicators $I_O$ obtained from a multitude of medical probes 302 previously operated with the generator 12. In the illustrated embodiment, a set of historical operational indicators $I_O$ are stored for each of the multitude of previously operated medical probes 302. Each set of historical operational indicators $I_O$ includes a probe identification code $C_I$ and supplementary historical operational indicators $I_{SO}$. Each probe identification code $C_I$ not only provides historical operational information about the respective medical probe 302, but also provides a means to cross-reference the supplementary historical operational indicators $I_{SO}$ within the respective set of historical operational indicators $I_O$, as will be described in further detail below.

The supplementary operational indicators $I_{SO}$ provide historical operational information concerning the operation of a medical probe 302, in addition to that provided by the presence of a cataloged probe identification code $C_I$. By way of non-limiting example, a supplementary operational indicator $I_O$ can be the initial probe usage time $T_I$ described previously above. Alternatively, a supplementary operational indicator $I_{SO}$ can be an incremental probe usage $U_I$, which represents the number of times a respective medical probe 302 has been operated. As will be described in further detail below, the historical operational indicators $I_{SO}$ can provide historical operational information of a selected medical probe 302 to a physician. The historical operational indicators $I_{SO}$ can be further used to conditionally operate the selected medical probe 302.

The catalog 122 is configured for retaining the probe historical operational indicators $I_O$, notwithstanding disconnection of the medical probe 302 from the generator 12. Thus, storage of the historical operational indicators $I_O$ within the catalog 122 for subsequent use obviates the need to store historical operational information within the medical probe 302 itself, thereby minimizing probe expense. For instance, absent the requirement to store historical operational information in the electronic storage componentry of the medical probe 302, a ROM or one or more resistors, which are relatively inexpensive, can be used as the probe identification component 50, merely for storage of the probe identification code $C_I$.

The control circuit 68 is configured for, upon connection of a selected medical probe 302 to the generator 12, reading the probe identification code $C_I$ from the probe identification component 50 of the selected medical probe 302. The control circuit 68 is further configured for, upon initial operation of the selected medical probe 302, storing the probe identification code $C_I$ in the catalog 122 as a historical operational indicator $I_O$, the presence of which indicates that the selected medical probe 302 has been previously operated with the generator 12.

The control circuit 68 is also configured for obtaining additional historical operational information concerning the operation of the selected medical probe 302, and storing this information in the catalog 122 as supplemental historical operational indicators $I_{SO}$. For instance, upon initial operation of the selected medical probe 302, the control circuit 68 can obtain the time of initial operation of the selected medical probe 302, which can then be stored in the catalog 122 as an initial probe usage time $T_I$ next to the probe identification code $C_I$ corresponding to the selected medical probe 302. Also, each time the selected medical probe 302 is operated, the control circuit 68 can obtain a cumulative number of times the selected medical probe 302 has been operated, which can then be stored in the catalog 122 as an incremental probe usage $U_I$ next to the probe identification code $C_I$ corresponding to the selected medical probe 302. Thus, a set of historical operational indicators $I_O$ for the selected medical probe 302 can be stored in the catalog 122.

The control circuit 68 is also configured for recalling historical operational information about a selected medical probe 302, which has been stored in the catalog 122 as the set of historical operational indicators $I_O$. In particular, the control circuit 68 can determine if the medical probe 302 has been previously operated with the generator 12 by determining if the probe identification code $C_I$ read from the medical probe 302 matches any of the probe identification codes $C_I$ stored in the catalog 122. The control circuit 68 can also determine additional historical operational information, such as, e.g., the initial time of operation of the medical probe 302 or the number of times the medical probe 302 has been previously operated, by obtaining the supplemental operational indicators $I_O$, associated with the matched probe identification code $C_I$. The recalled historical operational information can optionally be displayed on the display (not shown) for viewing by the physician.

The control circuit 68 is further configured for conditionally operating the selected medical probe 302, based on the set of historical operational indicators $I_O$ corresponding to the selected medical probe 302. That is, the control circuit 68 is configured for generating an interlock control signal $S_C$ based on the probe identification code $C_I$ and/or associated supplemental operational indicators $I_{SO}$. As will be discussed in further detail below, conditional operation of the medical probe 302 can not only be accomplished during the initial connection between the medical probe 302 and the generator 12, but can also be accomplished during reconnection between the medical probe 302 and the generator 12 (by recalling from the catalog 122), since the cataloged historical operational information is not lost upon disconnection of the medical probe 302 from the generator 12.

By way of non-limiting example, the control circuit 68 can conditionally operate the selected medical probe 302, based on the probe identification code $C_I$ and the probe sterilization indicator $I_S$, which is stored in the selected medical probe 302 and read out by the control circuit 68, as previously discussed above. In particular, as discussed above, a presence of the probe identification code $C_I$ in the catalog 122 indicates that the selected medical probe 302 has been previously operated. A presence of the probe sterilization indicator $I_S$ in the selected medical probe 302 indicates that the selected medical probe 302 has been previously sterilized. In this manner, use of the probe identification code $C_I$ allows a medical probe that has been legitimately sterilized by a post-manufacture process to be distinguished from a medical probe that has been illegitimately re-sterilized after usage. Upon operation of the selected medical probe 302, the control circuit 68 stores the probe identification code $C_I$ in the catalog 122 and clears the probe sterilization indicator $I_S$ from the selected medical probe 302, so that the selected medical probe 302 is not prematurely rendered inoperable through legitimate adjustment of the connection between the selected medical probe 302 and the generator 12.

Operation of the selected medical probe 302 is prevented if both the probe sterilization indicator $I_S$ and the probe identification code $C_I$ are present (indicating that the selected medical probe 302 has been re-sterilized), or if both the probe sterilization indicator $I_S$ and the probe identification code $C_I$ are not present (indicating that the selected medical probe 302 has never been sterilized). Operation of the selected medical probe 302 is allowed if the probe identification code $C_I$ is present and the probe identification code $C_I$ is not present (indicating that the medical probe has only been sterilized once and never operated), or the probe sterilization indicator $I_S$ is not present and the probe identification code $C_I$ is present (indicating that the medical probe has only been sterilized once and is currently being used in an initial procedure).

By way of further non-limiting example, the control circuit 68 can conditionally operate the selected medical probe 302, based on the initial probe usage time $T_I$ and the predetermined elapsed time limit $T_L$, which may be encoded in the probe identification code $C_I$ of the selected medical probe 302, as previously discussed above. Upon initial operation of the selected medical probe 302, the control circuit 68 stores the initial probe usage time $T_U$, along with the probe identification code $C_I$, in the catalog 122. The control circuit 68 prevents operation of the selected medical probe 302 when the predetermined elapsed time limit $T_L$ is expired. Expiration of the predetermined elapsed time limit $T_L$ occurs when the difference between the initial probe usage time $T_I$ and a reference time exceeds the predetermined elapsed time limit $T_L$.

By way of further non-limiting example, the control circuit 68 can conditionally operate the selected medical probe 302, based on the incremental probe usage $U_I$ and a predetermined maximum usage limit $U_L$, which may be encoded in the probe identification code $C_I$ of the selected medical probe 302. Upon initial operation of the selected medical probe 302, the control circuit 68 stores a "1" as the incremental probe usage $U_I$, along with the probe identification code $C_I$, in the catalog 122. Upon each subsequent operation of the selected medical probe 302, the control circuit 68 increments the incremental probe usage $U_I$ by one. The control circuit 68 prevents operation of the selected medical probe 302 when the incremental probe usage $U_I$ exceeds the predetermined maximum usage limit $U_L$.

Further details regarding the use of an incremental probe usage $U_I$ and a predetermined maximum usage limit $U_L$ is further disclosed in U.S. Pat. No. 5,383,874, entitled "Systems for Identifying Catheters and Monitoring Their Use," which issued Jan. 24, 1995, and which is hereby fully and expressly incorporated herein by reference.

Figure 9:
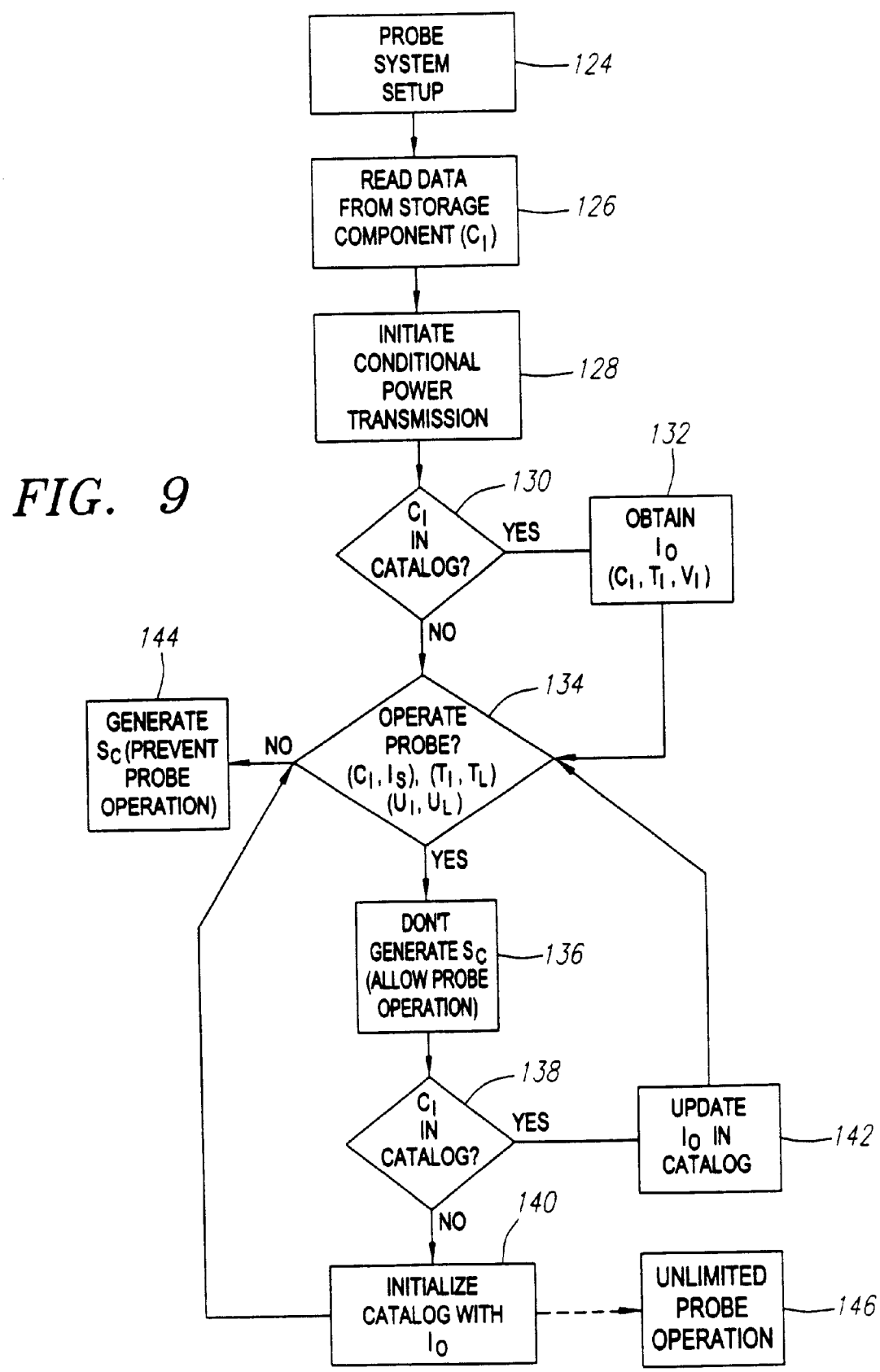
FIG. 9 is a flow diagram of a preferred method of obtaining historical operational information and conditionally operating the medical probe employed in the medical probe system of FIG. 7.

With reference to FIG. 9, operation of the medical probe system 300, in identifying and disabling re-used single use devices based on cataloging catheter usage, will now be described. The medical probe system 300 is set up by physically connecting a selected medical probe 302 (the historical operation of which is not known) to the generator 12 and powering on the generator 12 (step 124). At this point, the generator 12 is in standby mode. The generator 12 then reads the probe identification code $C_I$ from the probe identification component 50 of the selected medical probe 302, i.e., obtains the selected probe identification code $C_I$ (step 126). After insertion of the selected medical probe 302 within the patient's body and placement of the ablation electrode 16 in contact with the tissue to be ablated, the RF power control button 44 (shown in FIG. 1) is depressed to conditionally initiate power transmission from the generator 12 and subsequent delivery of RF energy to the tissue (step 128). At this point, the generator 12 is in delivery mode.

The generator 12 then obtains historical operational information for the selected medical probe 302 from the catalog 122 (steps 130–134). That is, the catalog 122 is searched to determine if the selected probe identification code $C_I$ matches a cataloged probe identification code C, (step 130). If the selected probe identification code $C_I$ does match a cataloged probe identification code $C_I$, the set of historical operational indicators $I_O$ associated with the matched identification code $C_I$ (i.e., the set of historical operational indicators $I_O$ corresponding to the selected medical probe 302) is obtained (step 132).

As discussed above, the set of historical operational indicators $I_O$ comprises the probe identification code $C_I$, the presence of which indicates that the selected medical probe 302 has been previously operated; the initial probe usage time $T_I$, indicating that time of initial operation of the selected medical probe 302; and the incremental probe usage $U_I$, indicating the number of times the selected medical probe 302 has been previously operated. This historical operational information can be optionally displayed on the display (not shown) for viewing by the physician.

If the selected probe identification code $C_I$ does not match a cataloged probe identification code $C_I$, the selected medical probe 302 is deemed to have not been previously operated, and a set of historical operational indicators $I_O$ corresponding to the selected medical probe 302 does not exist. This historical operational information can be optionally displayed on the display (not shown) for viewing by the physician.

The generator 12 then determines whether or not the selected medical probe 302 should be operated, based on the historical operational information obtained from the catalog 122 (step 134). For example, as discussed above, the generator 12 can conditionally operate the selected medical probe 302, based on the presence of the probe identification code $C_I$ in the catalog 122 and a presence of the probe sterilization indicator $I_S$ in the selected medical probe 302; and/or based on the initial probe usage time $T_I$ and the predetermined elapsed usage limit $T_L$; and/or the incremental probe usage $U_I$ and the predetermined maximum usage limit $U_L$.

If the generator 12 determines that the selected medical probe 302 can be operated, the generator 12 allows operation of the selected medical probe 302, i.e., the interlock control signal $S_C$ is not generated (step 136). If operation of the selected medical probe 302 is the first time that the selected medical probe 302 has been operated, i.e., if the selected probe identification code $C_I$ did not match a cataloged probe identification code $C_I$ (step 138), the catalog 122 is initialized with a set of historical operational indicators $I_O$ corresponding to the selected medical probe 302, based on the operation of the selected medical probe (step 140). That is, the selected probe identification code $C_I$, along with the time of initial operation and number of times the selected medical probe 302 has been operated (1 time in this case), is stored in the catalog 122.

In the illustrated embodiment, initialization of the catalog 122 with the set of historical operational indicators $I_O$ occurs upon effective operation of the medical probe 302, i.e., operation of the medical probe 302 in such a manner as to form a lesion on the tissue. In this regard, to prevent premature initialization of the catalog 122, the set of historical operational indicators $I_O$ is not stored in the catalog 122 during non-therapeutic operation of the medical probe 302, i.e., when faulty operation of the medical probe 302 does not result in a tissue lesion. Such faulty probe operation can be caused by a variety of reasons, including inadequate contact between the ablation electrode 16 and the tissue, inadequate energy delivery to the ablation electrode 16 and inadequate duration of energy application.

If operation of the selected medical probe 302 is not the first time that the selected medical probe 302 has been operated, i.e., if the selected probe identification code $C_I$ did match a cataloged probe identification code $C_I$ (step 138), the generator 12 updates the set of historical operational indicators $I_O$ corresponding to the selected medical probe 302 (step 142). For instance, the incremental probe usage $U_I$ may be incremented by one. If the generator 12 determines that the selected medical probe 302 cannot be operated (step 134), the generator 12 prevents operation of the selected medical probe 302, i.e., the interlock control signal $S_C$ is generated (step 144).

The generator 12 periodically determines (e.g., every second, when operation of the selected medical probe 302 is based on the initial probe usage time $T_I$, and every time the selected medical probe 302, when operation of the selected medical probe 302 is based on the incremental probe usage $U_I$) whether the selected medical probe 302 should be operated, and conditionally allows operation of the medical probe 302, based on the set of historical operational indicators $I_O$, until the selected medical probe 302 is disconnected from the generator 12 (steps 134–144). Alternatively, the generator 12 determines whether the selected medical probe 302 should be operated only one time per probe connection. That is, once operation of the selected medical probe 302 is allowed, the selected medical probe 302 can be operated without limitation until the selected medical probe 302 is physically disconnected from, and again connected to, the generator 12 (step 146).

Preventing Automatic Identification of Devices

Figure 10:
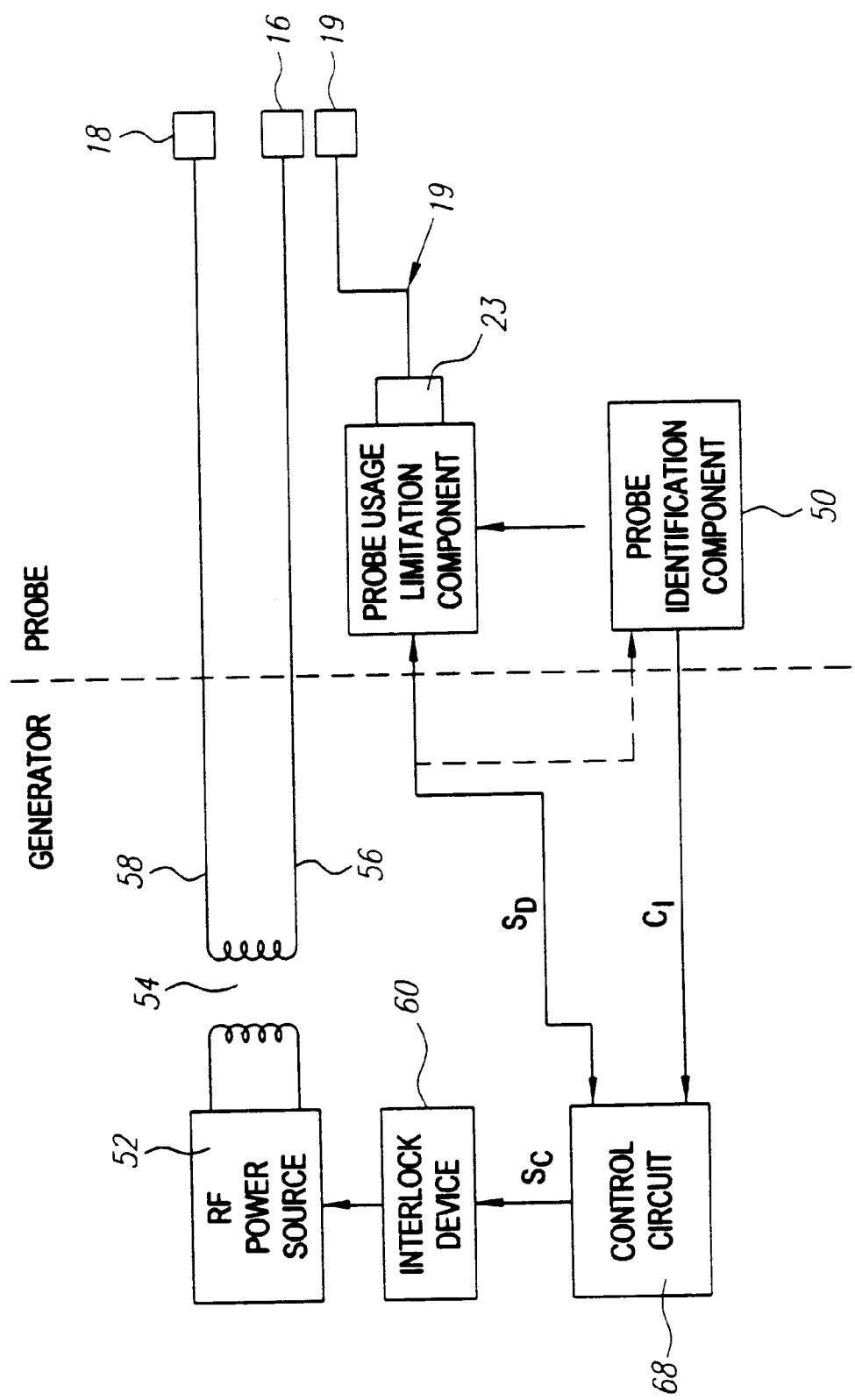
FIG. 10 is a schematic of still another alternative preferred embodiment of a medical probe system.

Referring to FIG. 10, the medical probe system 300 is alternatively capable of preventing automatic identification of re-used single use devices. In this regard, the probe usage limitation component 51 is a disabling circuit, the activation of which disables the probe identification component 50 by modifying the manner in which the probe identification component 50 functions. In the illustrated embodiment, the disabling circuit 51 is a switch that changes the output of the probe identification component 50. For example, if the probe identification component 50 comprises one or more resistors, the disabling circuit 51 can change the output resistance value seen by the generator 12 by shorting the output of the one or more resistors. Of course, if probe identification component 50 comprises a microchip, one or more pins of the microchip can be shorted to create the same effect.

Disablement of the probe identification component 50 prevents the correct probe identification code $C_I$ from being read therefrom, which, as will be discussed in further detail below, precludes the medical probe 302 from being operated. Prior to initial operation of the medical probe 302, the disabling circuit 51 is configured to enable the probe identification component 50. That is, the disabling circuit 51 provides an open circuit to the output of the probe identification component 50. A non-limiting example of a disabling circuit 51 is an electrolytic switch. Application of a disable signal $S_D$ on the disabling circuit 51 from an external source, i.e., the generator 12, activates the disabling circuit 51. Preferably, once the disabling circuit 51 is activated, disablement of the probe identification component 50 is continued even when the power is removed from the disabling circuit 51. In this manner, no generator 12 will be able to read the probe identification code $C_I$ from the probe identification component 50 after the probe identification component 50 has been disabled.

The control circuit 68 is configured for determining whether the medical probe 302 has been previously used, i.e., whether the medical probe 302 has been used to render a complete procedure on a patient. The control circuit 68 can determine whether the medical probe 302 has been previously used by employing a variety of techniques.

By way of non-limiting example, the control circuit 68 can base the determination of whether the medical probe 302 has been previously used on the time elapsed after an initial operation of the medical probe 302, as discussed above. In particular, upon initial operation of the medical probe 302, the control circuit 68 stores an initial probe usage time $T_I$ in the medical probe 302 (either in the probe identification component 50 or other electronic storage componentry), or in a catalog within the control circuit 68, along with the probe identification code $C_I$, which can then be later read out by the control circuit 68. The control circuit 68 then determines if a predetermined elapsed time limit $T_L$ (which may be encoded into the probe identification code $C_I$) has expired, i.e., if the difference between the initial probe usage time $T_I$ and a reference time exceeds the predetermined elapsed time limit $T_L$. The medical probe 302 is determined to have been previously used when the predetermined elapsed time limit $T_L$ has expired.

By way of further non-limiting example, the control circuit 68 can base the determination of whether the medical probe 302 has been previously used on a number of times the medical probe 302 has been operated, as discussed previously. In particular, upon initial operation of the medical probe 302, an incremental probe usage $U_I$ can be stored in the medical probe 302 (either in the probe identification component 50 or other electronic storage componentry), or a catalog, along with the probe identification code $C_I$, which can then be later read out by the control circuit 68. Each time the medical probe 302 is operated, i.e., each time power is applied to the medical probe 302, the control circuit 68 increments the incremental probe usage $U_I$ by one. The control circuit 68 then determines if the incremental probe usage $U_I$ exceeds a predetermined probe usage limit $U_L$ (which may be encoded into the probe identification code $C_I$). The medical probe 302 is determined to have been previously used when incremental probe usage $U_I$ exceeds the predetermined probe usage limit $U_L$.

By way of further non-limiting example, the control circuit 68 can base the determination of whether the medical probe 302 has been previously used on both a previous operation of the medical probe 302 and a previous sterilization of the medical probe 302, as discussed previously. In particular, upon initial operation of the medical probe 302, a probe usage indicator $I_U$ is stored in the medical probe 302 (either in the probe identification component 50 or other electronic storage componentry), or a catalog in the form of the probe identification code $C_I$, which can then be later read out by the control circuit 68. Upon sterilization of the medical probe 302, a probe sterilization indicator $I_S$ is stored in the medical probe 302, preferably in an environmentally sensing microchip, which can be later read out by the control circuit 68. In this manner, use of the probe identification code $C_I$ allows a medical probe that has been legitimately sterilized by a post-manufacture process to be distinguished from a medical probe that has been illegitimately re-sterilized after usage.

Upon operation of the medical probe 302, the control circuit 68 stores the probe identification code $C_I$ in the medical probe 302 or catalog 122 and clears the probe sterilization indicator $I_S$ from the medical probe 302 or catalog, so that the medical probe 302 is not prematurely rendered inoperable through legitimate adjustment of the connection between the medical probe 302 and the generator 12. The medical probe 302 is determined to have been previously used if both the probe sterilization indicator $I_S$ and the previous probe usage indicator $I_U$ are present (indicating that the medical probe 302 has been re-sterilized), or if both the probe sterilization indicator $I_S$ and the previous probe usage indicator $I_U$ are not present (indicating that the medical probe 302 has never been sterilized).

As will be discussed in further detail below, previous probe use can be periodically determined after connection of the medical probe 302 to the generator 12, but before disconnection of the medical probe 302 from the generator 12. Alternatively, previous probe use is only determined once upon connection of the medical probe 302 to the generator 12.

The control circuit 68 is further configured for generating the disable signal $S_D$ based on the determination of whether the medical probe 302 has been previously used. In particular, if the medical probe 302 is determined to have been previously used, the control circuit 68 generates the disable signal $S_D$, thereby activating the disabling circuit 51. As discussed above, activation of the disabling circuit 51 disables the probe identification component 50, thereby preventing the probe identification code $C_I$ from being read from the probe identification component 50. If the medical probe 302 is determined not to have been previously used, the control circuit 68 does not generate the disable signal $S_D$, thereby maintaining the inactivation of the disabling circuit 51. As discussed above, inactivation of the disabling circuit 51 enables the probe identification component 50, thereby allowing the correct probe identification code $C_I$ to be read from the probe identification component 50.

In alternative embodiments, the disabling circuit 51 can be eliminated by configuring the control circuit 68 to directly disable the probe identification component 50 by modifying the probe identification code $C_I$ in the probe identification component 50 (shown by dashed line). Preferably, this can be accomplished by clearing the probe identification code $C_I$ from the probe identification component 50. In this case, the probe identification component 50 preferably comprises a microchip, such as, e.g., an EEPROM, which is non-volatile, yet easily allows data to be written thereto. Alternatively, the probe identification component 50 can be a digital circuit that outputs a pulse train or a laser-trimmed clock. Even more alternatively, the probe identification component 50 can be a solid-state component, such as, e.g., a variable resistor, an array of resistors or a laser-trimmed resistor.

In further alternative embodiments, the disabling circuit 51 comprises a microprocessor that internally determines whether the medical probe 302 has been previously used (i.e., exclusive of a disable signal $S_D$ transmitted from the generator 12), and disables the probe identification component 50, based on this determination. The probe-based microprocessor can disable the probe identification component 50 by modifying the functioning of the probe identification component 50 itself, such as by shorting the probe identification component 50, or by modifying the probe identification code $C_I$ storage by the probe identification component 50, such as by clearing the probe identification code $C_I$ therefrom. In this manner, no additional processing need take place in the generator 12. Thus, a standard generator having the capability of reading a probe identification code from a medical probe and conditionally operating the medical probe based on the value of the probe identification code, can be used with the medical probe 302.

The probe-based microprocessor can sense power flow from the generator 12 during operation of the medical probe 302, thereby allowing the microprocessor to detect such probe usage parameters as previous probe operation, an initial time of probe operation, and a number of times of probe operation. The probe-based microprocessor may also have the capability of detecting sterilization of the medical probe 302. Thus, in this manner, the probe-based microprocessor can base the determination of whether the medical probe 302 has been previously operated on an elapsed time after an initial operation of the medical probe 302, on a number of times the medical probe 302 has been operated, or on a previous operation of the medical probe 302 and previous sterilization of the medical probe 302.

The control circuit 68 is further configured for reading the probe identification code $C_I$ from the probe identification component 50 when enabled. The control circuit 68 compares the probe identification code $C_I$ read from the probe identification component 50 with a look-up table of approved probe identification codes. If the probe identification code $C_I$ does not match any of the approved probe identification codes in the look-up table (either because the wrong medical probe is being used with the generator 12, or the probe identification code $C_I$ read by the control circuit 68 has been altered due to previous probe use), the control circuit 68 does not allow operation of the medical probe 302. That is, the control circuit 68 generates an interlock control signal $S_C$.

If the probe identification code $C_I$ does match any of the approved probe identification codes in the look-up table (because the right medical probe is used and the probe identification code $C_I$ read by the control circuit 68 has not been altered due to no previous probe use), the control circuit 68 allows operation of the medical probe 302. That is, the control circuit 68 does not generate an interlock control signal $S_C$. Further details regarding the conditional operation of a medical probe based on an automatic reading of a probe identification code is further disclosed in U.S. Pat. No. 5,383,874, which has previously been incorporated herein by reference.

The control circuit 68 is electrically coupled to the interlock device 60 and applies the interlock control signal $S_C$ thereto. Application of the interlock control signal $S_C$ activates the interlock device 60, preventing power from being outputted from the power source 52, and in turn, preventing subsequent conveyance of RF energy to tissue in contact with the ablation electrode 16.

Figure 11:
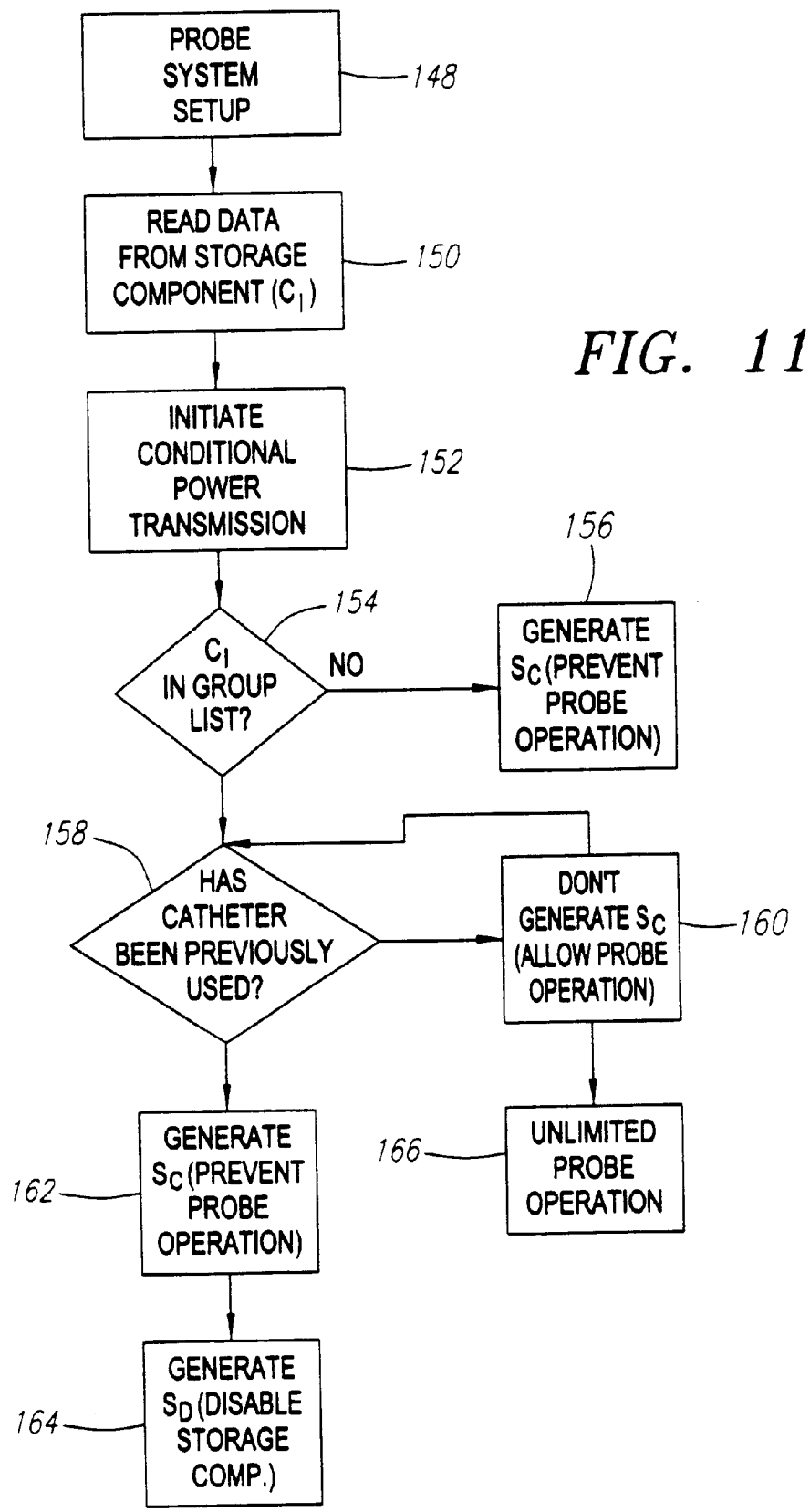
FIG. 11 is a flow diagram of a preferred method of conditionally operating a medical probe employed in the medical probe system of FIG. 10.

With reference to FIG. 11, operation of the medical probe system 300 will now be described. The medical probe system 300 is set up by physically connecting a medical probe 302 (the historical operation of which is not known) to the generator 12 and powering on the generator 12 (step 148). At this point, the generator 12 is in standby mode. The generator 12 then reads the probe identification code $C_I$ from the probe identification component 50 of the medical probe 302 (step 150). After insertion of the medical probe 302 within the patient's body and placement of the ablation electrode 16 in contact with the tissue to be ablated, the RF power control button 44 (shown in FIG. 1) is depressed to conditionally initiate power transmission from the generator 12 and subsequent delivery of RF energy to the tissue (step 152). At this point, the generator 12 is in delivery mode.

The generator 12 then determines if the probe identification code $C_I$ read from the probe identification component 50 matches an approved probe identification code located in the look-up list (step 154). If the probe identification code $C_I$ does not match an approved probe identification code (either because the medical probe 302 is not approved for use with the generator 12 or the probe identification component 50 located in the medical probe 302 has been disabled due to detection of previous probe usage), the generator 12 prevents operation of the medical probe 302, i.e., the interlock control signal $S_C$ is generated (step 156). It should be noted that, if the probe identification component 50 is disabled by shorting, or if the probe identification code $C_I$ is cleared from the probe identification component 50, the generator 12 will not be able to obtain a value from the probe identification component 50, in which case the generator 12 need not access the look-up list to ultimately determine that the medical probe 302 should not be operated.

If the probe identification code $C_I$ does match an approved probe identification code (because the medical probe 302 is approved for use with the generator 12 and had not been determined to have been previously used during a previous connection), the generator 12 determines if the medical probe 302 has been previously used based on, e.g., the presence of the probe identification code $C_I$ and the presence of the probe sterilization indicator $I_S$; and/or the initial probe usage time $T_I$ and the predetermined elapsed usage limit $T_L$; or the incremental probe usage $U_I$ and the predetermined maximum usage limit $U_L$, as discussed above (step 158).

If the medical probe 302 is determined not to have been previously used, the generator 12 allows operation of the medical probe 302, i.e., the interlock control signal $S_C$ is not generated (step 160). If the medical probe 302 is determined to have been previously used, the generator 12 prevents operation of the medical probe 302, i.e., the interlock control signal $S_C$ is generated (step 162). In addition, the generator 12 disables the probe identification component 50 in the medical probe 302 by transmitting the disable signal $S_D$ to the disabling circuit 51, or alternatively, by clearing the probe identification code $C_I$ from the probe identification component 50 (step 164). In this manner, when the medical probe 302 is reconnected to any generator that is configured to automatically read a probe identification code from a medical probe, including the generator 12, the generator quickly determines that the medical probe 302 has been previously used, and thus prevents the operation thereof (step 156).

The generator 12 periodically determines (e.g., every second, when operation of the medical probe 302 is based on the initial probe usage time $T_I$, and every time the medical probe 302, when operation of the medical probe 302 is based on the incremental probe usage $U_I$) whether the medical probe 302 has been previously used, and conditionally allows operation of the medical probe 302, while also conditionally disabling the probe identification component 50, based on this determination, until the medical probe 302 is disconnected from the generator 12 (steps 158–164). The control circuit 68 can periodically determine whether the medical probe 302 has been determined to have been previously used by periodically reading the probe identification code $C_I$ from the probe identification component 50, and comparing to the approved probe identification codes in the look-up list.

Alternatively, the generator 12 determines whether the medical probe 302 should be operated only one time per probe connection. That is, once operation of the medical probe 302 is allowed, the medical probe 302 can be operated without limitation until the medical probe 302 is physically disconnected from, and again connected to, the generator 12 (step 166).

Limiting Re-Use of Multiple Use Devices

Operation of the medical probe system 300 has been described above as limiting re-use of single use medical probes 302. The medical probe system 300, however, can be employed to limit re-usage of multiple use medical probes 302 as well. By way of non-limiting example, the medical probe system 300 can comprise a counter that keeps track of the number of times the medical probe 302 is indicated as being used. If the counter reaches a maximum limit, the medical probe 302 is prevented from being operated.

If the medical probe system 300 limits re-usage of the multiple use medical probe 302 based on the initial time that a medical probe 302 is therapeutically used, the previous initial probe usage time $T_I$ is cleared and a current initial probe usage time $T_I$ is stored each time the maximum predetermined elapsed time limit $T_L$ expires. The counter, preferably located in the medical probe 302, keeps track of the number of times the maximum predetermined elapsed time limit $T_L$ expires. The medical probe system 300 prevents further usage of the medical probe 302 once the maximum predetermined elapsed time limit $T_L$ has expired and once the counter has reached a predetermined limit. For example, if the number of uses of the medical probe 302 is to be limited to five, operation of the medical probe 302 may be prevented after the counter reaches five.

If the medical probe system 300 limits re-usage of a multiple use medical probe 302 based on detecting environmental changes, the probe sterilization indicator $I_S$ is cleared each time the medical probe 302 is therapeutically used and restored each time the medical probe 302 is sterilized. The counter, preferably located in the medical probe 302, keeps track of the number of times the presence of the probe sterilization indicator $I_S$ is detected upon operation of the medical probe 302. The medical probe system 300 prevents further usage of the medical probe 302 once the presence of both the probe sterilization indicator $I_S$ and the previous probe usage indicator $I_U$ is detected, and the counter has reached a predetermined limit.

Similarly, counters can be employed by the medical probe system 300 in limited re-usage of multiple use medical probes 302 based on cataloging probe usage, in which case multiple counters are preferably located in the RF generator 12 to respectively keep track of a multiple number of medical probes 302. Or a counter can be employed by the medical probe system 300 in limiting re-usage of a medical probe 302 by preventing automatic identification of the medical probe 302, in which case the counter is preferably located in the medical probe 302.

It should further be noted that all of the above-described methods of limiting re-use of a medical probe can each be employed alone to provide a single level safety measure, or alternatively, in combination, to provide a multiple level safety measure.

While preferred methods and embodiments have been shown and described, it will be apparent to one of ordinary skill in the art that numerous alterations may be made without departing from the spirit or scope of the invention. Therefore, the invention is not to be limited except in accordance with the following claims.

What is claimed is:

1. A method of limiting usage of a medical probe, the medical probe including an electronic storage component for storing a probe identification code, the method comprising:

determining if the medical probe has been previously used; and modifying the probe identification code if the medical probe is determined to have been previously used.

2. The method of claim 1, wherein the probe identification code is modified by clearing the correct probe identification code from the electronic storage component.

3. The method of claim 1, wherein the determination of whether the medical probe has been previously used is based on an elapsed time since an initial operation of the medical probe.

4. The method of claim 1, wherein the determination of whether the medical probe has been previously used is based on a number of times the medical probe has been operated.

5. The method of claim 1, wherein the determination of whether the medical probe has been previously used in based on determining whether there has been a previous operation of the medical probe and a sterilization of the medical probe.

6. The method of claim 1, wherein the probe identification code is a unique serial number.

7. The method of claim 1, wherein the probe identification code identifies a characteristic of the medical probe.

8. A medical probe, comprising:

an elongate member having a distally located functional component;

an electronic storage component mounted to the elongate member, the electronic storage component having stored therein a correct probe identification code; and disabling circuitry mounted to the elongate member, the disabling circuitry being electrically coupled to the electronic storage component, and being configured for detecting whether the medical probe has been previously used, and for disabling the electronic storage component if the medical probe is determined to have been previously used.

9. The medical probe of claim 8, wherein the disabling circuitry disables the electronic storage component by shorting the electronic storage component.

10. The medical probe of claim 8, wherein the electronic storage component comprises one or more resistors.

11. The medical probe of claim 8, wherein the electronic storage component comprises a semiconductor device.

12. The medical probe of claim 8, wherein the disabling circuitry detects whether the medical probe has been previously used by sensing a disable signal transmitted from a source external to the medical probe.

13. The medical probe of claim 8, wherein the probe identification code is a unique serial number.

14. The medical probe of claim 8, wherein the probe identification code identifies a characteristic of the medical probe.

15. The medical probe of claim 8, wherein the elongate member forms a catheter.

16. The medical probe of claim 8, wherein the elongate member forms a surgical probe.

17. A control unit for connection to a medical probe, the medical probe having an electronic storage component for storing a probe identification code, the control unit comprising:

control circuitry configured to electrically couple to the electronic storage component for determining if the medical probe has been previously used, and for modifying the probe identification code if the medical probe is determined to have been previously used.

18. The control unit of claim 17, wherein the determination of whether the medical probe has been previously used is based on an elapsed time since an initial operation of the medical probe.

19. The control unit of claim 17, wherein the determination of whether the medical probe has been previously used is based on a number of times the medical probe has been operated.

20. The control unit of claim 17, wherein the determination of whether the medical probe has been previously used in based on determining whether that has been an initial operation and sterilization of the medical probe.

21. The control unit of claim 17, wherein the probe identification code is a unique serial number.

22. The control unit of claim 17, wherein the control circuitry comprises a microprocessor.

23. The control unit of claim 17, further comprising:

an RF power source; and an interlocking device electrically coupled between the RF power source and the control circuit.

* * * * *